United States Patent
Ito et al.

(10) Patent No.: US 10,570,248 B2
(45) Date of Patent: Feb. 25, 2020

(54) CURED FILM FORMATION COMPOSITION, ORIENTATION MATERIAL, AND RETARDATION MATERIAL

(71) Applicant: NISSAN CHEMICAL INDUSTRIES, LTD., Tokyo (JP)

(72) Inventors: Jun Ito, Funabashi (JP); Yuta Kanno, Funabashi (JP); Tadashi Hatanaka, Funabashi (JP)

(73) Assignee: NISSAN CHEMICAL INDUSTRIES, LTD., Tokyo (JP)

( * ) Notice: Subject to any disclaimer, the term of this patent is extended or adjusted under 35 U.S.C. 154(b) by 0 days.

(21) Appl. No.: 15/558,172

(22) PCT Filed: Mar. 9, 2016

(86) PCT No.: PCT/JP2016/057423
§ 371 (c)(1),
(2) Date: Sep. 13, 2017

(87) PCT Pub. No.: WO2016/147987
PCT Pub. Date: Sep. 22, 2016

(65) Prior Publication Data
US 2018/0112032 A1   Apr. 26, 2018

(30) Foreign Application Priority Data

Mar. 13, 2015  (JP) ................. 2015-051446

(51) Int. Cl.
| | | |
|---|---|---|
| C08G 59/16 | (2006.01) | |
| C09D 163/10 | (2006.01) | |
| G02F 1/1337 | (2006.01) | |
| C08G 59/62 | (2006.01) | |
| G02F 1/13363 | (2006.01) | |
| C09D 7/40 | (2018.01) | |
| C08G 59/40 | (2006.01) | |
| C09D 201/00 | (2006.01) | |
| C08G 59/50 | (2006.01) | |
| C08G 81/02 | (2006.01) | |
| C09D 163/00 | (2006.01) | |
| C09D 187/00 | (2006.01) | |
| G02B 5/30 | (2006.01) | |
| C07C 67/26 | (2006.01) | |
| C07C 69/65 | (2006.01) | |
| C07C 69/618 | (2006.01) | |
| C07C 69/734 | (2006.01) | |

(52) U.S. Cl.
CPC ....... *C08G 59/628* (2013.01); *C08G 59/1455* (2013.01); *C08G 59/1461* (2013.01); *C08G 59/40* (2013.01); *C08G 59/5086* (2013.01); *C08G 81/027* (2013.01); *C09D 7/40* (2018.01); *C09D 163/00* (2013.01); *C09D 163/10* (2013.01); *C09D 187/005* (2013.01); *C09D 201/00* (2013.01); *G02B 5/3016* (2013.01); *G02F 1/1337* (2013.01); *G02F 1/13363* (2013.01); *C07C 67/26* (2013.01); *C07C 69/618* (2013.01); *C07C 69/65* (2013.01); *C07C 69/734* (2013.01); *G02F 2001/133633* (2013.01); *G02F 2413/01* (2013.01); *G02F 2413/05* (2013.01)

(58) Field of Classification Search
None
See application file for complete search history.

(56) References Cited

U.S. PATENT DOCUMENTS

| | | | | |
|---|---|---|---|---|
| 5,512,607 A * | 4/1996 | Kinashi | ................. | G03F 7/0388 522/100 |
| 6,156,479 A * | 12/2000 | Meador | .................... | C08F 8/00 430/270.1 |
| 2001/0053437 A1* | 12/2001 | Sato | .................. | C08G 59/1461 428/209 |
| 2014/0182903 A1* | 7/2014 | Sagara | ................... | B32B 15/08 174/255 |
| 2016/0222248 A1* | 8/2016 | Endo | ....................... | B05D 1/38 |

FOREIGN PATENT DOCUMENTS

| | | |
|---|---|---|
| JP | H10-232365 A | 9/1998 |
| JP | 2001-517719 A | 10/2001 |

(Continued)

OTHER PUBLICATIONS

Jacobs, Durable Glossy, Matte and Wrinkle Finish Powder Coatings . . . ; Progress in Organic Coatings 29 (1996) p. 127-138. (Year: 1996).*

(Continued)

*Primary Examiner* — David J Buttner
(74) *Attorney, Agent, or Firm* — Oliff PLC

(57) ABSTRACT

A cured-film formation composition that forms a cured film exhibiting excellent liquid-crystal orientation properties and excellent light transmission properties when the cured-film formation composition is used as an orientation material and a layer of a polymerizable liquid crystal is arranged thereon. A cured-film formation composition including a component (A) that is a compound obtained by reacting a cinnamic acid compound of Formula (1) below with a compound having at least one epoxy group in one molecule,

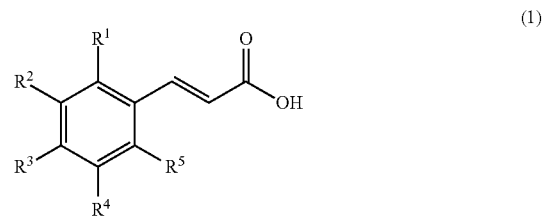

(1)

wherein $R^1$, $R^2$, $R^3$, $R^4$, and $R^5$ are each independently a substituent selected from a hydrogen atom, a halogen atom, a $C_{1-6}$ alkyl, a $C_{1-6}$ haloalkyl, a $C_{1-6}$ alkoxy, a $C_{1-6}$ haloalkoxy, cyano, and nitro; and a component (B) that is a cross-linking agent, an orientation material which is obtained from the composition, and a retardation material which is obtained from the composition.

9 Claims, No Drawings

(56) References Cited

FOREIGN PATENT DOCUMENTS

| | | |
|---|---|---|
| JP | 3611342 B2 | 1/2005 |
| JP | 2005-049865 A | 2/2005 |
| JP | 2009-058584 A | 3/2009 |
| JP | 2014-56103 A | 3/2014 |
| JP | 2015-31823 A | 2/2015 |
| JP | 2015031823 * | 2/2015 |
| WO | 2014/065324 A1 | 5/2014 |
| WO | 2014/136889 A1 | 9/2014 |
| WO | WO 2015/041208 * | 3/2015 |

OTHER PUBLICATIONS

TRiiSO KUKDO EPOXY product guide pp. 6-31 (no date). (Year: 000).*

May 9, 2018 Office Action issued in European Patent Application No. 16764817.9.

May 24, 2016 Written Opinion issued in International Patent Application No. PCT/JP2016/057423.

* cited by examiner

CURED FILM FORMATION COMPOSITION, ORIENTATION MATERIAL, AND RETARDATION MATERIAL

TECHNICAL FIELD

The present invention relates to a cured-film formation composition, an orientation material, and a retardation material.

BACKGROUND ART

Recently, in the field of displays such as televisions including liquid crystal panels, 3D displays with which 3D images can be enjoyed have been developed as efforts toward the high performance. In such 3D displays, a stereoscopic image can be displayed by, for example, causing the right eye of a viewer to see an image for the right eye and causing the left eye of the viewer see an image for the left eye.

Various 3D display methods for displaying 3D images can be used, and examples of the methods known as methods requiring no special eyeglasses include a lenticular lens method and a parallax barrier method.

As one of display methods for viewers to see 3D images with eyeglasses, a circularly polarized light glasses method, for example, is known (see Patent Document 1, for example).

In a 3D display using the circularly polarized light glasses method, a retardation material is generally arranged on a display element for forming an image of a liquid crystal panel and the like. In this retardation material, two types of retardation regions having different retardation characteristics are regularly arranged each in plurality to constitute a retardation material that is patterned. In the present specification, a retardation material thus patterned in which a plurality of retardation regions having different retardation characteristics are arranged is called a patterned retardation material hereinafter.

The patterned retardation material can be fabricated by optically patterning a retardation substance including a polymerizable liquid crystal as disclosed in Patent Document 2, for example. In the optical patterning of the retardation substance including a polymerizable liquid crystal, a photo-orientation technique known for forming an orientation material for a liquid crystal panel is used. More specifically, a coating made of a material having photo-orientation properties is provided on a substrate, and two types of polarized beams the polarization directions of which are different are radiated on this coating. Thus, a photo-orientation film is obtained as an orientation material in which two types of liquid crystal orientation regions are formed and the directions of orientation control of liquid crystals in the regions are different. Onto this photo-orientation film, a retardation substance containing a polymerizable liquid crystal in a solution state is applied to perform orientation of the polymerizable liquid crystal. Subsequently, the polymerizable liquid crystal thus oriented is cured to form a patterned retardation material.

As substances having photo-orientation properties that can be used in orientation material formation using a photo-orientation technique for liquid crystal panels, an acrylic resin and a polyimide resin, for example, are known that have in a side chain thereof a photodimerized moiety such as cinnamoyl group and chalcone group, for example. It is reported that these resins exhibit a property of controlling orientation of liquid crystals (hereinafter, also called liquid crystal orientation properties) by polarized UV irradiation (see Patent Document 3 to Patent Document 5).

PRIOR-ART DOCUMENTS

Patent Documents

Patent Document 1: Japanese Patent Application Publication No. 10-232365
Patent Document 2: Japanese Patent Application Publication No. 2005-49865
Patent Document 3: Japanese Patent No. 3,611,342
Patent Document 4: Japanese Patent Application Publication No. 2009-058584
Patent Document 5: Published Japanese Translation of PCT Application No. 2001-517719

SUMMARY OF THE INVENTION

Problems to be Solved by the Invention

As described above, the patterned retardation material is formed by laminating a layer of a cured polymerizable liquid crystal on a photo-orientation film being an orientation material. The patterned retardation material having such a laminate structure can be used to form a 3D display, in the laminated state without being processed.

Accordingly, a cured film that can be used as an orientation material excellent in both of liquid-crystal orientation properties and light transmission properties, and a cured-film formation composition for forming the cured film need to be developed.

The present invention has been made based on the above-described findings and study results. An object of the present invention is to provide a cured-film formation composition that is suitable to form a cured film having excellent liquid-crystal orientation properties and excellent light transmission properties. In particular, an object of the present invention is to provide a cured-film formation composition that forms a cured film exhibiting excellent liquid-crystal orientation properties and excellent light transmission properties when the cured-film formation composition is used as an orientation material and a layer of a polymerizable liquid crystal is arranged thereon.

An object of the present invention is to provide an orientation material excellent in liquid-crystal orientation properties and light transmission properties.

An object of the present invention is to provide a retardation material that can be optically patterned with high precision.

Other objects and advantages of the present invention will be apparent from the following description.

Means for Solving the Problems

As a result of repeated intensive studies to achieve the objects described above, the inventors have found that, by selecting a cured-film formation substance based on a compound (A) obtained by causing a specific cinnamic acid compound to react with a compound having at least one epoxy group in one molecule, a cured film having excellent orientation properties on any type of a substrate can be formed, and thus, the inventors have completed the present invention.

That is, the present invention relates to, as a first aspect, a cured-film formation composition comprising:

a component (A) that is a compound obtained by reacting a cinnamic acid compound of Formula (1) below with a compound having at least one epoxy group in one molecule,

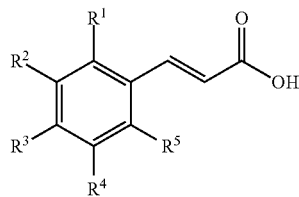

(1)

(wherein $R^1$, $R^2$, $R^3$, $R^4$, and $R^5$ are each independently a substituent selected from a hydrogen atom, a halogen atom, a $C_{1-6}$ alkyl, a $C_{1-6}$ haloalkyl, a $C_{1-6}$ alkoxy, a $C_{1-6}$ haloalkoxy, a $C_{3-8}$ cycloalkyl, a $C_{3-8}$ halocycloalkyl, a $C_{2-6}$ alkenyl, a $C_{2-6}$ haloalkenyl, a $C_{3-8}$ cycloalkenyl, a $C_{3-8}$ halocycloalkenyl, a $C_{2-6}$ alkynyl, a $C_{2-6}$ haloalkynyl, a ($C_{1-6}$ alkyl) carbonyl, a ($C_{1-6}$ haloalkyl) carbonyl, a ($C_{1-6}$ alkoxy) carbonyl, a ($C_{1-6}$ haloalkoxy) carbonyl, a ($C_{1-6}$ alkylamino) carbonyl, a ($C_{1-6}$ haloalkyl) aminocarbonyl, a di($C_{1-6}$ alkyl) aminocarbonyl, cyano, and nitro); and a component (B) that is a cross-linking agent.

As a second aspect, the present invention relates to the cured-film formation composition according to the first aspect, in which the cross-linking agent as the component (B) is a cross-linking agent having a methylol group or an alkoxymethyl group.

As a third aspect, the present invention relates to the cured-film formation composition according to the first aspect or the second aspect, the composition further comprising a component (C) that is a polymer having a thermally cross-linkable group.

As a fourth aspect, the present invention relates to the cured-film formation composition according to any one of the first aspect to the third aspect, the composition further comprising a component (D) that is a cross-linking catalyst.

As a fifth aspect, the present invention relates to the cured-film formation composition according to any one of the first aspect to the fourth aspect, the composition containing the component (B) in an amount of 1 part by mass to 600 parts by mass based on 100 parts by mass of the component (A).

As a sixth aspect, the present invention relates to the cured-film formation composition according to any one of the third aspect to the fifth aspect, the composition containing the component (C) in an amount of 1 part by mass to 400 parts by mass based on 100 parts by mass of the total amount of the component (A) and the component (B) as a cross-linking agent.

As a seventh aspect, the present invention relates to the cured-film formation composition according to any one of the fourth aspect to the sixth aspect, the composition containing the component (D) in an amount of 0.01 part by mass to 20 parts by mass based on 100 parts by mass of the total amount of the component (A) and the component (B) as a cross-linking agent.

As an eighth aspect, the present invention relates to a cured film characterized by being a cured product of the cured-film formation composition according to any one of the first aspect to the seventh aspect.

As a ninth aspect, the present invention relates to an orientation material characterized by being a cured product of the cured-film formation composition according to any one of the first aspect to the seventh aspect.

As a tenth aspect, the present invention relates to a retardation material formed by using a cured film obtained from the cured-film formation composition according to any one of the first aspect to the seventh aspect.

Effects of the Invention

According to the present invention, a cured film having excellent liquid-crystal orientation properties and excellent light transmission properties, and a cured-film formation composition suitable for forming the cured film can be provided.

According to the present invention, an orientation material that has excellent liquid crystal orientation properties and light transmission properties can be provided.

According to the present invention, a retardation material that can be optically patterned with high precision can be provided.

MODES FOR CARRYING OUT THE INVENTION

<Cured-Film Formation Composition>

A cured-film formation composition of the present invention comprises: a component (A) that is a compound obtained by causing a specific cinnamic acid compound to react with a compound having at least one epoxy group in one molecule; and a component (B) that is a cross-linking agent. In addition to the component (A) and the component (B), the cured-film formation composition of the present invention may further comprise a polymer having a thermally cross-linkable group as a component (C). The cured-film formation composition may further comprise a cross-linking catalyst as a component (D). The cured-film formation composition may further comprise a component that enhances the adhesive properties of a cured film formed as a component (E) (hereinafter, referred to as an adhesion enhancing component). Unless the effects of the present invention are impaired, the cured-film formation composition may further comprise a solvent and other additives.

Hereinafter, the details of each component will be described.

<Component (A)>

The component (A) contained in the cured-film formation composition of the present invention is a compound obtained by causing a cinnamic acid compound of Formula (1) to react with a compound having at least one epoxy group in one molecule.

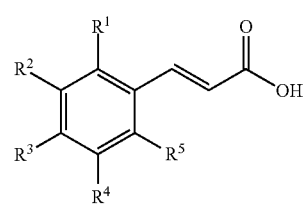

(1)

(In the formula, $R^1$, $R^2$, $R^3$, $R^4$, and $R^5$ are each independently a substituent selected from a hydrogen atom, a halogen atom, a $C_{1-6}$ alkyl, a $C_{1-6}$ haloalkyl, a $C_{1-6}$ alkoxy, a $C_{1-6}$ haloalkoxy, a $C_{3-8}$ cycloalkyl, a $C_{3-8}$ halocycloalkyl, a $C_{2-6}$ alkenyl, a $C_{2-6}$ haloalkenyl, a $C_{3-8}$ cycloalkenyl, a $C_{3-8}$ halocycloalkenyl, a $C_{2-6}$ alkynyl, a $C_{2-6}$ haloalkynyl, a ($C_{1-6}$ alkyl) carbonyl, a ($C_{1-6}$ haloalkyl) carbonyl, a ($C_{1-6}$ alkoxy) carbonyl, a ($C_{1-6}$ haloalkoxy) carbonyl, a ($C_{1-6}$ alkylamino) carbonyl, a ($C_{1-6}$ haloalkyl) aminocarbonyl, a di($C_{1-6}$ alkyl) aminocarbonyl, cyano, and nitro.)

Examples of the halogen atom in the present specification include a fluorine atom, a chlorine atom, a bromine atom, and an iodine atom. It should be noted that "halo" in the present specification also represents these halogen atoms.

In the present specification, a $C_{a-b}$ alkyl is a linear or branched hydrocarbon group having a carbon atom number of a to b. Specific examples of the $C_{a-b}$ alkyl include methyl group, ethyl group, n-propyl group, i-propyl group, n-butyl group, i-butyl group, s-butyl group, t-butyl group, n-pentyl group, 1-methylbutyl group, 2-methylbutyl group, 3-methylbutyl group, 1-ethylpropyl group, 1,1-dimethylpropyl group, 1,2-dimethylpropyl group, 2,2-dimethylpropyl group, n-hexyl group, 1-methylpentyl group, 2-methylpentyl group, 1,1-dimethylbutyl group, 1,3-dimethylbutyl group, heptyl group, octyl group, nonyl group, decyl group, undecyl group, and dodecyl group. The $C_{a-b}$ alkyl is selected in the range of the individual specified number of carbon atoms.

In the present specification, a $C_{a-b}$ haloalkyl is a linear or branched hydrocarbon group having a carbon atom number of a to b in which a hydrogen atom bonded to a carbon atom is arbitrarily substituted with a halogen atom. Here, when the hydrogen atom is substituted with two or more halogen atoms, these halogen atoms may be the same as or different from each other. Specific examples of the $C_{a-b}$ haloalkyl include fluoromethyl group, chloromethyl group, bromomethyl group, iodomethyl group, difluoromethyl group, chlorofluoromethyl group, dichloromethyl group, bromofluoromethyl group, trifluoromethyl group, chlorodifluoromethyl group, dichlorofluoromethyl group, trichloromethyl group, bromodifluoromethyl group, bromochlorofluoromethyl group, dibromofluoromethyl group, 2-fluoroethyl group, 2-chloroethyl group, 2-bromoethyl group, 2,2-difluoroethyl group, 2-chloro-2-fluoroethyl group, 2,2-dichloroethyl group, 2-bromo-2-fluoroethyl group, 2,2,2-trifluoroethyl group, 2-chloro-2,2-difluoroethyl group, 2,2-dichloro-2-fluoroethyl group, 2,2,2-trichloroethyl group, 2-bromo-2,2-difluoroethyl group, 2-bromo-2-chloro-2-fluoroethyl group, 2-bromo-2,2-dichloroethyl group, 1,1,2,2-tetrafluoroethyl group, pentafluoroethyl group, 1-chloro-1,2,2,2-tetrafluoroethyl group, 2-chloro-1,1,2,2-tetrafluoroethyl group, 1,2-dichloro-1,2,2-trifluoroethyl group, 2-bromo-1,1,2,2-tetrafluoroethyl group, 2-fluoropropyl group, 2-chloropropyl group, 2-bromopropyl group, 2-chloro-2-fluoropropyl group, 2,3-dichloropropyl group, 2-bromo-3-fluoropropyl group, 3-bromo-2-chloropropyl group, 2,3-dibromopropyl group, 3,3,3-trifluoropropyl group, 3-bromo-3,3-difluoropropyl group, 2,2,3,3-tetrafluoropropyl group, 2-chloro-3,3,3-trifluoropropyl group, 2,2,3,3,3-pentafluoropropyl group, 1,1,2,3,3,3-hexafluoropropyl group, heptafluoropropyl group, 2,3-dichloro-1,1,2,3,3-pentafluoropropyl group, 2-fluoro-1-methylethyl group, 2-chloro-1-methylethyl group, 2-bromo-1-methylethyl group, 2,2,2-trifluoro-1-(trifluoromethyl)ethyl group, 1,2,2,2-tetrafluoro-1-(trifluoromethyl)ethyl group, 2,2,3,3,4,4-hexafluorobutyl group, 2,2,3,4,4,4-hexafluorobutyl group, 2,2,3,3,4,4,4-heptafluorobutyl group, 1,1,2,2,3,3,4,4-octafluorobutyl group, nonafluorobutyl group, 4-chloro-1,1,2,2,3,3,4,4-octafluorobutyl group, 2-fluoro-2-methylpropyl group, 2-chloro-1,1-dimethylethyl group, 2-bromo-1,1-dimethylethyl group, 5-chloro-2,2,3,4,4,5,5-heptafluoropentyl group, and tridecafluorohexyl group. The $C_{a-b}$ haloalkyl is selected in the range of the individual specified number of carbon atoms.

In the present specification, a $C_{a-b}$ cycloalkyl is a cyclic hydrocarbon group having a carbon atom number of a to b in which a 3- to 6-membered monocyclic or polycyclic structure can be formed. The ring of each group may be optionally substituted with an alkyl group in a range of the specified number of carbon atoms. Specific examples of the $C_{a-b}$ cycloalkyl include cyclopropyl group, 1-methylcyclopropyl group, 2-methylcyclopropyl group, 2,2-dimethylcyclopropyl group, 2,2,3,3-tetramethylcyclopropyl group, cyclobutyl group, cyclopentyl group, 2-methylcyclopentyl group, 3-methylcyclopentyl group, cyclohexyl group, 2-methylcyclohexyl group, 3-methylcyclohexyl group, 4-methylcyclohexyl group, and bicyclo[2.2.1]heptan-2-yl group. The $C_{a-b}$ cycloalkyl is selected in the range of the individual specified number of carbon atoms.

In the present specification, a $C_{a-b}$ halocycloalkyl is a cyclic hydrocarbon group having a carbon atom number of a to b in which a hydrogen atom bonded to a carbon atom is arbitrarily substituted with a halogen atom and a 3- to 6-membered monocyclic or polycyclic structure can be formed. The ring of each group may be optionally substituted with an alkyl group in a range of the specified number of carbon atoms. The substitution with a halogen atom may be at a ring structure portion, at a side chain portion, or at both of these portions. Furthermore, in the case of the substitution with two or more halogen atoms, these halogen atoms may be the same as or different from each other. Specific examples of the $C_{a-b}$ halocycloalkyl include 2,2-difluorocyclopropyl group, 2,2-dichlorocyclopropyl group, 2,2-dibromocyclopropyl group, 2,2-difluoro-1-methylcyclopropyl group, 2,2-dichloro-1-methylcyclopropyl group, 2,2-dibromo-1-methylcyclopropyl group, 2,2,3,3-tetrafluorocyclobutyl group, 2-(trifluoromethyl)cyclohexyl group, 3-(trifluoromethyl)cyclohexyl group, and 4-(trifluoromethyl)cyclohexyl group. The $C_{a-b}$ halocycloalkyl is selected in the range of the individual specified number of carbon atoms.

In the present specification, a $C_{a-b}$ alkenyl is a linear or branched unsaturated hydrocarbon group having a carbon atom number of a to b and having one or two or more double bonds in a molecule. Specific examples of the $C_{a-b}$ alkenyl include vinyl group, 1-propenyl group, 2-propenyl group, 1-methylethenyl group, 2-butenyl group, 1-methyl-2-propenyl group, 2-methyl-2-propenyl group, 2-pentenyl group, 2-methyl-2-butenyl group, 3-methyl-2-butenyl group, 2-ethyl-2-propenyl group, 1,1-dimethyl-2-propenyl group, 2-hexenyl group, 2-methyl-2-pentenyl group, 2,4-dimethyl-2,6-heptadienyl group, and 3,7-dimethyl-2,6-octadienyl group. The $C_{a-b}$ alkenyl is selected in the range of the individual specified number of carbon atoms.

In the present specification, a $C_{a-b}$ haloalkenyl is a linear or branched unsaturated hydrocarbon group having a carbon atom number of a to b and having one or two or more double bonds in a molecule, in which a hydrogen atom bonded to a carbon atom is arbitrarily substituted with a halogen atom. Here, when the hydrogen atom is substituted with two or more halogen atoms, these halogen atoms may be the same as or different from each other. Specific examples of the $C_{a-b}$ haloalkenyl include 2,2-dichlorovinyl group, 2-fluoro-2-propenyl group, 2-chloro-2-propenyl group, 3-chloro-2-propenyl group, 2-bromo-2-propenyl group, 3-bromo-2-propenyl group, 3,3-difluoro-2-propenyl group, 2,3-dichloro-2-propenyl group, 3,3-dichloro-2-propenyl group, 2,3-dibromo-2-propenyl group, 2,3,3-trifluoro-2-propenyl group, 2,3,3-trichloro-2-propenyl group, 1-(trifluoromethyl)ethenyl group, 3-chloro-2-butenyl group, 3-bromo-2-butenyl group, 4,4-difluoro-3-butenyl group, 3,4,4-trifluoro-3-butenyl group, 3-chloro-4,4,4-trifluoro-2-butenyl group, and 3-bromo-2-methyl-2-propenyl group. The $C_{a-b}$ haloalkenyl is selected in the range of the individual specified number of carbon atoms.

In the present specification, a $C_{a-b}$ cycloalkenyl is a cyclic unsaturated hydrocarbon group having a carbon atom number of a to b and having one or two or more double bonds in which a 3- to 6-membered monocyclic or polycyclic structure can be formed. The ring of each group may be optionally substituted with an alkyl group in a range of the specified number of carbon atoms. Furthermore, the double bond(s) may be in the endo- or exo-form. Specific examples of the $C_{a-b}$ cycloalkenyl include 2-cyclopenten-1-yl group, 3-cyclopenten-1-yl group, 2-cyclohexen-1-yl group, 3-cyclohexen-1-yl group and bicyclo[2.2.1]-5-heptan-2-yl group. The $C_{a-b}$ cycloalkenyl is selected in the range of the individual specified number of carbon atoms.

In the present specification, a $C_{a-b}$ halocycloalkenyl is a cyclic unsaturated hydrocarbon group having a carbon atom number of a to b and having one or two or more double bonds in which a hydrogen atom bonded to a carbon atom is arbitrarily substituted with a halogen atom, and a 3- to 6-membered monocyclic or polycyclic structure can be formed. The ring of each group may be optionally substituted with an alkyl group in a range of the specified number of carbon atoms. Furthermore, the double bond(s) may be in the endo- or exo-form. The substitution with a halogen atom may be at a ring structure portion, at a side chain portion, or at both of these portions. In the case of the substitution with two or more halogen atoms, these halogen atoms may be the same as or different from each other. Specific examples of the $C_{a-b}$ halocycloalkenyl include 2-chlorobicyclo[2.2.1]-5-hepten-2-yl group. The $C_{a-b}$ halocycloalkenyl is selected in the range of the individual specified number of carbon atoms.

In the present specification, a $C_{a-b}$ alkynyl is a linear or branched unsaturated hydrocarbon group having a carbon atom number of a to b and having one or two or more triple bonds in a molecule. Specific examples of the $C_{a-b}$ alkynyl include ethynyl group, 1-propynyl group, 2-propynyl group, 2-butynyl group, 1-methyl-2-propynyl group, 2-pentynyl group, 1-methyl-2-butynyl group, 1,1-dimethyl-2-propynyl group, and 2-hexynyl group. The $C_{a-b}$ alkynyl is selected in the range of the individual specified number of carbon atoms.

In the present specification, a $C_{a-b}$ haloalkynyl is a linear or branched unsaturated hydrocarbon group having a carbon atom number of a to b and having one or two or more triple bonds in a molecule, in which a hydrogen atom bonded to a carbon atom is arbitrarily substituted with a halogen atom. Here, in the case of the substitution with two or more halogen atoms, these halogen atoms may be the same as or different from each other. Specific examples of the $C_{a-b}$ haloalkynyl include 2-chloroethynyl group, 2-bromoethynyl group, 2-iodoethynyl group, 3-chloro-2-propynyl group, 3-bromo-2-propynyl group, and 3-iodo-2-propynyl group. The $C_{a-b}$ haloalkynyl is selected in the range of the individual specified number of carbon atoms.

In the present specification, a $C_{a-b}$ alkoxy is an alkyl-O— group in which the alkyl has a carbon atom number of a to b and has the above-described meaning. Specific examples of the $C_{a-b}$ alkoxy include methoxy group, ethoxy group, n-propyloxy group, i-propyloxy group, n-butyloxy group, i-butyloxy group, s-butyloxy group, t-butyloxy group, n-pentyloxy group, and n-hexyloxy group. The $C_{a-b}$ alkoxy is selected in the range of the individual specified number of carbon atoms.

In the present specification, a $C_{a-b}$ haloalkoxy is a haloalkyl-O— group in which the haloalkyl has a carbon atom number of a to b and has the above-described meaning. Specific examples of the $C_{a-b}$ haloalkoxy include difluoromethoxy group, trifluoromethoxy group, chlorodifluoromethoxy group, bromodifluoromethoxy group, 2-fluoroethoxy group, 2-chloroethoxy group, 2,2,2-trifluoroethoxy group, 1,1,2,2-tetrafluoroethoxy group, 2-chloro-1,1,2-trifluoroethoxy group, 2-bromo-1,1,2-trifluoroethoxy group, pentafluoroethoxy group, 2,2-dichloro-1,1,2-trifluoroethoxy group, 2,2,2-trichloro-1,1-difluoroethoxy group, 2-bromo-1,1,2,2-tetrafluoroethoxy group, 2,2,3,3-tetrafluoropropyloxy group, 1,1,2,3,3,3-hexafluoropropyloxy group, 2,2,2-trifluoro-1-(trifluoromethyl)ethoxy group, heptafluoropropyloxy group, and 2-bromo-1,1,2,3,3,3-hexafluoropropyloxy group. The $C_{a-b}$ haloalkoxy is selected in the range of the individual specified number of carbon atoms.

In the present specification, a ($C_{a-b}$ alkyl) carbonyl is an alkyl-C(O)— group in which the alkyl has a carbon atom number of a to b and has the above-described meaning. Specific examples of the ($C_{a-b}$ alkyl) carbonyl include acetyl group, propionyl group, butyryl group, isobutyryl group, valeryl group, isovaleryl group, 2-methylbutanoyl group, pivaloyl group, hexanoyl group, and heptanoyl group. The ($C_{a-b}$ alkyl) carbonyl is selected in the range of the individual specified number of carbon atoms.

In the present specification, a ($C_{a-b}$ haloalkyl) carbonyl is a haloalkyl-C(O)— group in which the haloalkyl has a carbon atom number of a to b and has the above-described meaning. Specific examples of the ($C_{a-b}$ haloalkyl) carbonyl include fluoroacetyl group, chloroacetyl group, difluoroacetyl group, dichloroacetyl group, trifluoroacetyl group, chlorodifluoroacetyl group, bromodifluoroacetyl group, trichloroacetyl group, pentafluoropropionyl group, heptafluorobutanoyl group, and 3-chloro-2,2-dimethylpropanoyl group. The ($C_{a-b}$ haloalkyl) carbonyl is selected in the range of the individual specified number of carbon atoms.

In the present specification, a ($C_{a-b}$ alkoxy) carbonyl is an alkyl-O—C(O)— group in which the alkyl has a carbon atom number of a to b and has the above-described meaning. Specific examples of the ($C_{a-b}$ alkoxy) carbonyl include methoxycarbonyl group, ethoxycarbonyl group, n-propyloxycarbonyl group, i-propyloxycarbonyl group, n-butoxycarbonyl group, i-butoxycarbonyl group, and t-butoxycarbonyl group. The ($C_{a-b}$ alkoxy) carbonyl is selected in the range of the individual specified number of carbon atoms.

In the present specification, a ($C_{a-b}$ haloalkoxy) carbonyl is a haloalkyl-O—C(O)— group in which the haloalkyl has a carbon atom number of a to b and has the above-described meaning. Specific examples of the ($C_{a-b}$ haloalkoxy) carbonyl include 2-chloroethoxycarbonyl group, 2,2-difluoroethoxycarbonyl group, 2,2,2-trifluoroethoxycarbonyl group, and 2,2,2-trichloroethoxycarbonyl group. The ($C_{a-b}$ haloalkoxy) carbonyl is selected in the range of the individual specified number of carbon atoms.

In the present specification, a ($C_{a-b}$ alkylamino) carbonyl is a carbamoyl group in which one hydrogen atom is substituted with an alkyl group having a carbon atom number of a to b and having the above-described meaning. Specific examples of the ($C_{a-b}$ alkylamino) carbonyl include methylcarbamoyl group, ethylcarbamoyl group, n-propylcarbamoyl group, i-propylcarbamoyl group, n-butylcarbamoyl group, i-butylcarbamoyl group, s-butylcarbamoyl group, and t-butylcarbamoyl group. The ($C_{a-b}$ alkylamino) carbonyl is selected in the range of the individual specified number of carbon atoms.

In the present specification, a ($C_{a-b}$ haloalkylamino) carbonyl is a carbamoyl group in which one hydrogen atom is substituted with a haloalkyl group having a carbon atom number of a to b and having the above-described meaning. Specific examples of the ($C_{a-b}$ haloalkylamino) carbonyl include 2-fluoroethylcarbamoyl group, 2-chloroethylcarbamoyl group, 2,2-difluoroethylcarbamoyl group, and 2,2, 2-trifluoroethylcarbamoyl group. The ($C_{a-b}$ haloalkylamino) carbonyl is selected in the range of the individual specified number of carbon atoms.

In the present specification, a di($C_{a-b}$ alkyl)aminocarbonyl is a carbamoyl group in which both hydrogen atoms are substituted with individual alkyl groups, the alkyl groups each having a carbon atom number of a to b and being the same as or different from each other and having the above-described meaning. Specific examples of the di($C_{a-b}$ alkyl) aminocarbonyl include N,N-dimethylcarbamoyl group, N-ethyl-N-methylcarbamoyl group, N,N-diethylcarbamoyl group, N,N-di-n-propylcarbamoyl group, and N,N-di-n-butylcarbamoyl group. The di($C_{a-b}$ alkyl)aminocarbonyl is selected in the range of the individual specified number of carbon atoms.

The substituents $R^1$, $R^2$, $R^3$, $R^4$, and $R^5$ of the cinnamic acid compound of Formula (1) are, among the groups recited above, each independently preferably a substituent selected from a hydrogen atom, a halogen atom, a $C_{1-6}$ alkyl, a $C_{1-6}$ haloalkyl, a $C_{1-6}$ alkoxy, a $C_{1-6}$ haloalkoxy, cyano, and nitro.

Furthermore, from the viewpoint of orientation sensitivity, $R^3$ is preferably a substitutent selected from the substitutents defined above, other than hydrogen atom, and more preferably a substitutent selected from a halogen atom, a $C_{1-6}$ alkyl, a $C_{1-6}$ haloalkyl, a $C_{1-6}$ alkoxy, a $C_{1-6}$ haloalkoxy, cyano, and nitro.

Examples of the compound having at least one epoxy group in one molecule include compounds having a molecular weight of 100 to 5,000.

Examples of a monoepoxy compound as the compound having at least one epoxy group in one molecule include, but not limited to, butyl glycidyl ether, hexyl glycidyl ether, phenyl glycidyl ether, p-xylyl glycidyl ether, allyl glycidyl ether, p-tert-butylphenyl glycidyl ether, ethylene oxide, propylene oxide, epoxy pentane, epoxy butane, epichlorohydrin, epibromohydrin, glycidol (oxilanylmethanol), glycidyl acetate, glycidyl butyrate, glycidyl hexoate, glycidyl benzoate, pentamethylene oxide, epoxycyclopentane, and epoxycyclohexane.

Examples of an epoxy compound having two or more epoxy groups as the compound having at least one epoxy group in one molecule include, but not limited to, tris(2,3-epoxypropyl)isocyanurate, 1,4-butanediol diglycidyl ether, 1,2-epoxy-4-(epoxyethyl)cyclohexane, glycerol triglycidyl ether, diethylene glycol diglycidyl ether, 2,6-diglycidyl phenyl glycidyl ether, 1,1,3-tris[p-(2,3-epoxypropoxy)phenyl] propane, 1,2-cyclohexanedicarboxylic acid diglycidyl ester, 4,4'-methylenebis(N,N-diglycidyl aniline), 3,4-epoxycyclohexylmethyl-3,4-epoxycyclohexane carboxylate, trimethylolethane triglycidyl ether, bisphenol A-diglycidyl ether, and a pentaerythritol polyglycidyl ether.

Furthermore, commercially available compounds may be employed because of their easy availability. Specific examples (trade names) of the commercially available compounds include, but not limited to: epoxy resins having amino group, such as YH-434 and YH434L (manufactured by Tohto Kasei Co., Ltd.); epoxy resins having a cyclohexene oxide structure, such as Epolead GT-401, Epolead GT-403, Epolead GT-301, Epolead GT-302, Celloxide 2021, and Celloxide 3000 (manufactured by DAICEL CORPORATION); bisphenol A epoxy resins, such as jER (registered trademark) 1001, jER 1002, jER 1003, jER 1004, jER 1007, and jER 828 (manufactured by Mitsubishi Chemical Corporation); bisphenol F epoxy resins, such as EPIKOTE 807 (manufactured by Yuka-Shell Epoxy Co., Ltd. (the present Japan Epoxy Resins Co., Ltd.)); cycloaliphatic epoxy resins, such as DENACOL EX-252 (manufactured by Nagase ChemteX Corporation), CY175, CY177, CYI79, Araldite CY-182, Araldite CY-192, and Araldite CY-184 (manufactured by CIBA-GEIGY A.G), EPICLON 200 and EPICLON 400 (manufactured by Dainippon Ink and Chemicals, Inc. (the present DIC Corporation)), jER (registered trademark) 871 and jER 872 (manufactured by Japan Epoxy Resins Co., Ltd.), and ED-5661 and ED-5662 (manufactured by Celanese Coating Company); aliphatic polyglycidyl ethers, such as DENACOL EX-611, DENACOL EX-612, DENACOL EX-614, DENACOL EX-622, DENACOL EX-411, DENACOL EX-512, DENACOL EX-522, DENACOL EX-421, DENACOL EX-313, DENACOL EX-314, and DENACOL EX-321 (manufactured by Nagase ChemteX Corporation); and TEPIC (registered trademark) (manufactured by Nissan Chemical Industries, Ltd).

As the compound having at least one epoxy group in one molecule, a compound having two or more epoxy groups in one molecule is preferably employed from the viewpoint of cross-linkage formation.

To obtain a compound as the component (A) by causing the cinnamic acid compound of Formula (1) to react with the above-mentioned epoxy compound, the cinnamic acid compound of Formula (1) may be allowed to react in an amount of 1 to 1.2 equivalents to an epoxy group(s) of the epoxy compound in an organic solvent at room temperature. Examples of the organic solvent for this reaction include solvents to be described in <Solvent> below.

Alternatively, in the present invention, a mixture of a plurality of types of the above-mentioned compounds may be employed as the compound having at least one epoxy group in one molecule that is used for the component (A).

<Component (B)>

The component (B) in the cured-film formation composition of the present invention is a cross-linking agent.

The cross-linking agent serving as the component (B) is preferably a cross-linking agent having a group, such as a methylol group or an alkoxymethyl group, that forms a cross-linkage with a thermally cross-linkable functional group of the component (A).

Examples of the compound having such a group include methylol compounds, such as an alkoxymethylated glycoluril, an alkoxymethylated benzoguanamine, and alkoxymethylated melamine.

It should be noted that the thermally cross-linkable functional group of the component (A) is principally a hydroxy group.

Specific examples of the alkoxymethylated glycoluril include 1,3,4,6-tetrakis(methoxymethyl)glycoluril, 1,3,4,6-tetrakis(butoxymethyl)glycoluril, 1,3,4,6-tetrakis(hydroxymethyl)glycoluril, 1,3-bis(hydroxymethyl)urea, 1,1,3,3-tetrakis(butoxymethyl)urea, 1,1,3,3-tetrakis (methoxymethyl)urea, 1,3-bis(hydroxymethyl)-4,5-dihydroxy-2-imidazolinone, and 1,3-bis(methoxymethyl)-4,5-dimethoxy-2-imidazolinone. Examples of commercially available products of the alkoxymethylated glycoluril include: compounds such as glycoluril compounds (trade name: Cymel (registered trademark) 1170, Powderlink (registered trademark) 1174), a methylated urea resin (trade name: UFR (registered trademark) 65), and butylated urea resins (trade name: UFR (registered trademark) 300, U-VAN 10S60, U-VAN 10R, and U-VAN 11HV), manufactured by Nihon Cytec Industries Inc. (the former Mitsui Cytec Ltd.); and urea/formaldehyde-based resins (highly condensed-type, trade name: Beckamine (registered trademark) J-300S, Beckamine P-955, and Beckamine N) manufactured by DIC corporation (the former Dainippon Ink and Chemicals, Inc.).

Specific examples of the alkoxymethylated benzoguanamine include tetramethoxymethyl benzoguanamine. Examples of commercially available products of the alkoxymethylated benzoguanamine include a product (trade name: Cymel (registered trademark) 1123) manufactured by Nihon Cytec Industries Inc. (the former Mitsui Cytec Ltd.), and products (trade name: NIKALAC (registered trademark) BX-4000, NIKALAC BX-37, NIKALAC BL-60, and NIKALAC BX-55H) manufactured by Sanwa Chemical Co., Ltd.

Specific examples of the alkoxymethylated melamine include hexamethoxymethyl melamine. Examples of commercially available products of the alkoxymethylated melamine include methoxymethyl-type melamine compounds (trade name: Cymel (registered trademark) 300, Cymel 301, Cymel 303, and Cymel 350) and butoxymethyl-type melamine compounds (trade name: Mycoat (registered trademark) 506, and Mycoat 508), manufactured by Nihon Cytec Industries Inc. (the former Mitsui Cytec Ltd.); and methoxymethyl-type melamine compounds (trade name: NIKALAC (registered trademark) MW-30, NIKALAC MW-22, NIKALAC MW-11, NIKALAC MS-001, NIKALAC MX-002, NIKALAC MX-730, NIKALAC MX-750, and NIKALAC MX-035) and butoxymethyl-type melamine compounds (trade name: NIKALAC (registered trademark) MX-45, NIKALAC MX-410, and NIKALAC MX-302), manufactured by Sanwa Chemical Co., Ltd.

The cross-linking agent as the component (B) may also be a compound obtained by condensing a melamine compound, a urea compound, a glycoluril compound, or a benzoguanamine compound in which a hydrogen atom of amino group is substituted with a methylol group or an alkoxymethyl group. Examples of such compounds include a high-molecular-weight compound produced from a melamine compound and a benzoguanamine compound described in U.S. Pat. No. 6,323,310. Examples of commercially available products of the melamine compound include a product trade-named Cymel (registered trademark) 303 (manufactured by Nihon Cytec Industries Inc. (the former Mitsui Cytec Ltd)). Examples of commercially available products of the benzoguanamine compound include a product trade-named Cymel (registered trademark) 1123 (manufactured by Nihon Cytec Industries Inc. (the former Mitsui Cytec Ltd)).

Alternatively, as the cross-linking agent of the component (B), a polymer produced by using an acrylamide compound or a methacrylamide compound in which a hydrogen atom is substituted with a hydroxymethyl group (that is, methylol group) or an alkoxymethyl group, such as N-hydroxymethyl acrylamide, N-methoxymethyl methacrylamide, N-ethoxymethyl acrylamide, and N-butoxymethyl methacrylamide may be used.

Examples of such polymer include a poly(N-butoxymethyl acrylamide), a copolymer of N-butoxymethyl acrylamide and styrene, a copolymer of N-hydroxymethyl methacrylamide and methyl methacrylate, a copolymer of N-ethoxymethyl methacrylamide and benzyl methacrylate, and a copolymer of N-butoxymethyl acrylamide, benzyl methacrylate and 2-hydroxypropyl methacrylate. Such polymer preferably has a weight-average molecular weight (in terms of polystyrene) of 1,000 to 500,000, preferably 2,000 to 200,000, more preferably 3,000 to 150,000, and still more preferably 3,000 to 50,000.

These cross-linking agents may be used alone, or two or more of them may be used in combination. Further examples of the component (13) include a polymer (hereinafter, referred to as a specific copolymer 2) having an N-alkoxymethyl group and a side chain group containing a polymerizable C=C double bond as a unit structure.

Examples of a nitrogen atom N of the N-alkoxymethyl group include a nitrogen atom of amide, a nitrogen atom of thioamide, a nitrogen atom of urea, a nitrogen atom of thiourea, a nitrogen atom of urethane, and a nitrogen atom bonded to a vicinal position of a nitrogen atom of a nitrogen-containing hetero ring. Accordingly, examples of the N-alkoxymethyl group include a group having a structure in which an alkoxymethyl group is bonded to a nitrogen atom selected from a nitrogen atom of amide, a nitrogen atom of thioamide, a nitrogen atom of urea, a nitrogen atom of thiourea, a nitrogen atom of urethane, and a nitrogen atom bonded to a vicinal position of a nitrogen atom of a nitrogen-containing hetero ring.

The provision of imparting the N-alkoxymethyl group to the specific copolymer 2 is achieved by using a monomer that provides the N-alkoxymethyl group (hereinafter, referred to as a specific monomer X1) in polymerization.

The monomer that provides the N-alkoxymethyl group is not limited to a particular monomer as long as the monomer has the N-alkoxymethyl group, but, for example, a compound of the following Formula (X1) is preferably employed.

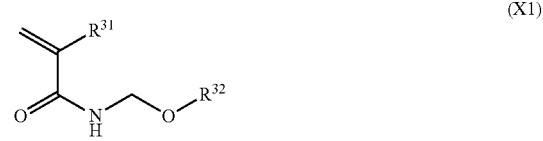

(X1)

(In the formula, $R^{31}$ is a hydrogen atom or methyl group, and $R^{32}$ is a hydrogen atom or a linear or branched $C_{1-10}$ alkyl group.)

Examples of the alkyl group include methyl group, ethyl group, n-propyl group, isopropyl group, n-butyl group, isobutyl group, sec-butyl group, tert-butyl group, n-pentyl group, 1-methyl-n-butyl group, 2-methyl-n-butyl group, 3-methyl-n-butyl group, 1,1-dimethyl-n-propyl group, 1,2-dimethyl-n-propyl group, 2,2-dimethyl-n-propyl group, 1-ethyl-n-propyl group, n-hexyl group, 1-methyl-n-pentyl group, 2-methyl-n-pentyl group, 3-methyl-n-pentyl group, 4-methyl-n-pentyl group, 1,1-dimethyl-n-butyl group, 1,2-dimethyl-n-butyl group, 1,3-dimethyl-n-butyl group, 2,2-dimethyl-n-butyl group, 2,3-dimethyl-n-butyl group, 3,3-dimethyl-n-butyl group, 1-ethyl-n-butyl group, 2-ethyl-n-butyl group, 1,1,2-trimethyl-n-propyl group, 1,2,2-trimethyl-n-propyl group, 1-ethyl-1-methyl-n-propyl group, 1-ethyl-2-methyl-n-propyl group, n-heptyl group, 1-methyl-n-hexyl group, 2-methyl-n-hexyl group, 3-methyl-n-hexyl group, 1,1-dimethyl-n-pentyl group, 1,2-dimethyl-n-pentyl group, 1,3-dimethyl-n-pentyl group, 2,2-dimethyl-n-pentyl group, 2,3-dimethyl-n-pentyl group, 3,3-dimethyl-n-pentyl group, 1-ethyl-n-pentyl group, 2-ethyl-n-pentyl group, 3-ethyl-n-pentyl group, 1-methyl-1-ethyl-n-butyl group, 1-methyl-2-ethyl-n-butyl group, 1-ethyl-2-methyl-n-butyl group, 2-methyl-2-ethyl-n-butyl group, 2-ethyl-3-methyl-n- butyl group, n-octyl group, 1-methyl-n-heptyl group, 2-methyl-n-heptyl group, 3-methyl-n-heptyl group, 1,1-dimethyl-n-hexyl group, 1,2-dimethyl-n-hexyl group, 1,3-dimethyl-n-hexyl group, 2,2-dimethyl-n-hexyl group, 2,3-dimethyl-n-hexyl group, 3,3-dimethyl-n-hexyl group, 1-ethyl-n-hexyl group, 2-ethyl-n-hexyl group, 3-ethyl-n-hexyl group, 1-methyl-1-ethyl-n-pentyl group, 1-methyl-2-ethyl-n-pentyl group, 1-methyl-3-ethyl-n-pentyl group, 2-methyl-2-ethyl-n-pentyl group, 2-methyl-3-ethyl-n-pentyl group, 3-methyl-3-ethyl-n-pentyl group, n-nonyl group, and n-decyl group.

Specific examples of the compound of Formula (X1) above include acrylamide compounds and methacrylamide compounds in each of which a hydrogen atom is substituted with a hydroxymethyl group or an alkoxymethyl group, such as N-hydroxymethyl (meth)acrylamide, N-methoxy methyl (meth)acrylamide, N-ethoxymethyl (meth)acrylamide, and N-butoxymethyl (meth)acrylamide. It should be noted that (meth)acrylamide means both methacrylamide and acrylamide.

Examples of the side chain group containing a polymerizable C═C double bond include acrylic group, methacrylic group, vinyl group, allyl group, and maleimide group.

Further examples of the side chain group containing a polymerizable C═C double bond include a $C_{3-16}$ organic group having a polymerizable C═C double bond at a terminal thereof, and particularly, a side chain group of Formula (b2) is preferable. The side chain group of Formula (b2) is to be bonded to an ester bond portion of an acrylic polymer, as illustrated in Formula (b2-1).

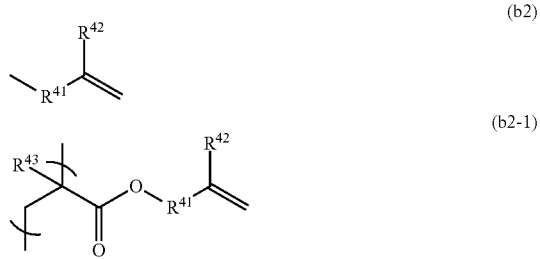

In Formula (b2), $R^{41}$ is a $C_{1-14}$ organic group selected from the group consisting of an aliphatic group, an aliphatic group containing a cyclic structure, and an aromatic group; or an organic group formed of a combination of a plurality of organic groups selected from the above-mentioned groups. $R^{41}$ may have an ester bond, an ether bond, an amide bond, or a urethane bond.

In Formula (b2), $R^{42}$ is a hydrogen atom or methyl group. A side chain group in which $R^{42}$ is a hydrogen atom is preferable, and a side chain group having an acryloyl group, a methacryloyl group, or a styryl group at a terminal thereof is more preferable.

In Formula (b2-1), $R^{43}$ is a hydrogen atom or methyl group.

The process for obtaining the polymer having the side chain group is not limited to a particular process. One example of such process is such that, by a polymerization process such as radical polymerization, an acrylic polymer having a specific functional group is produced in advance. Next, by causing this specific functional group to react with a compound (hereinafter, referred to as a specific compound) having a functional group that has a polymerizable C═C double bond at a terminal thereof and reacts with the above-mentioned specific functional group to form a bond, a side chain group is formed, whereby the side chain group containing the polymerizable C═C double bond is introduced into the specific copolymer 2.

The specific functional group herein is a functional group, such as carboxy group, glycidyl group, hydroxy group, amino group having active hydrogen, a phenolic hydroxy group, or an isocyanate group; or a plurality of types of the functional groups selected from these groups.

In the above-mentioned reaction to form the side chain group, a preferable combination of the specific functional group and the functional group with which the specific functional group of the specific compound reacts to form a bond is, for example, a combination of carboxy group and epoxy group, a combination of hydroxy group and isocyanate group, a combination of phenolic hydroxy group and epoxy group, a combination of carboxy group and isocyanate group, a combination of amino group and isocyanate group, or a combination of hydroxy group and an acid chloride. A more preferable combination is a combination of carboxy group and glycidyl methacrylate or a combination of hydroxy group and isocyanatoethyl methacrylate.

Furthermore, in the above-mentioned reaction to form the side chain group, the polymer having the specific functional group is a copolymer obtained by polymerizing a monomer having the specific functional group (hereinafter, referred to as a specific monomer X3), that is, a monomer having, for example, a carboxy group, a glycidyl group, a hydroxy group, an amino group having active hydrogen, a phenolic hydroxy group, or an isocyanate group, in addition to the monomer that provides the N-alkoxymethyl group (the specific monomer X1), and the polymer preferably has a number average molecular weight of 2,000 to 25,000. Here, the monomer having the specific functional group and being to be used for the polymerization may be used alone, or a plurality of types of the functional groups may be used in combination as long as the combination causes no reaction during the polymerization.

Specific examples of a monomer necessary to obtain the polymer having the specific functional group, that is, the specific monomer X3 will be given below. It should be noted that the specific monomer X3 is not limited to these examples.

Examples of the monomer having a carboxy group include acrylic acid, methacrylic acid, crotonic acid, mono-(2-(acryloyloxy)ethyl)phthalate, mono-(2-(methacryloyloxy)ethyl)phthalate, N-(carboxyphenyl)maleimide, N-(carboxyphenyl)methacrylamide, and N-(carboxyphenyl)acrylamide.

Examples of the monomer having a glycidyl group include glycidyl methacrylate, glycidyl acrylate, allyl glycidyl ether, 3-ethenyl-7-oxabicyclo[4.1.0]heptane, 1,2-epoxy-5-hexene, and 1,7-octadiene mono epoxide.

Examples of the monomer having a hydroxy group include 2-hydroxyethyl acrylate, 2-hydroxyethyl methacrylate, 2-hydroxypropyl acrylate, 2-hydroxypropyl methacrylate, 4-hydroxybutyl acrylate, 4-hydroxybutyl methacrylate, 2,3-dihydroxypropyl acrylate, 2,3-dihydroxypropyl methacrylate, diethylene glycol monoacrylate, diethylene glycol monomethacrylate, caprolactone 2-(acryloyloxy)ethyl ester, caprolactone 2-(methacryloyloxy)ethyl ester, a poly(ethylene glycol)ethylether acrylate, a poly(ethylene glycol)ethylether methacrylate, a 5-acryloyloxy-6-hydroxynorbornene-2-carboxylic-6-lactone, and a 5-methacryloyloxy-6-hydroxynorbornene-2-carboxylic-6-lactone.

Examples of the monomer having an amino group include 2-aminoethyl acrylate and 2-aminomethyl methacrylate.

Examples of the monomer having a phenolic hydroxy group include hydroxystyrene, N-(hydroxyphenyl) acrylamide, N-(hydroxyphenyl) methacrylamide, and N-(hydroxyphenyl) maleimide.

Examples of the monomer having an isocyanate group include acryloylethyl isocyanate, methacryloylethyl isocyanate, and m-tetramethyl xylene isocyanate.

Specific examples of $R^{41}$ in the thus-obtained side chain of Formula (b2) include groups of Formula (B-1) to Formula (B-11) below.

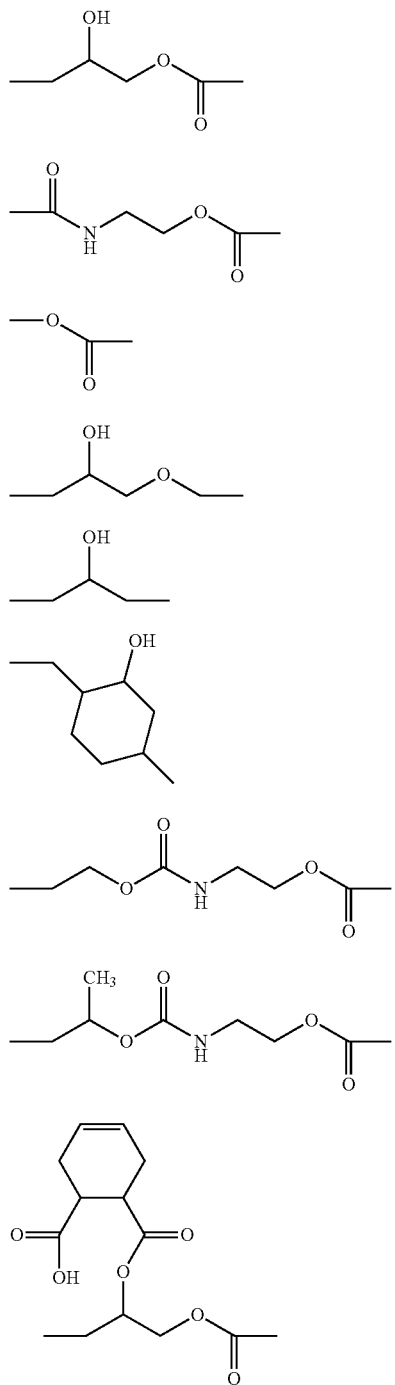

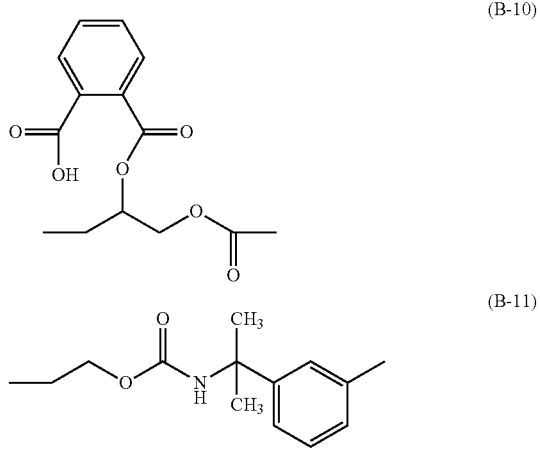

In the present invention, to obtain the polymer (the specific copolymer 2) as an example of the component (B), in addition to the specific monomer X1 and the specific monomer X3, another monomer copolymerizable with said specific monomers and not having the above-mentioned thermally cross-linkable substituent may be used.

Specific examples of such monomer (hereinafter, also referred to as a monomer X4) include an acrylic acid ester compound and a methacrylic acid ester compound, a maleimide compound, an acrylamide compound, acrylonitrile, maleic anhydride, a styrene compound, and a vinyl compound, each having a different structure from structures of the specific monomer X1 and the specific monomer X3.

Specific examples of the monomer X4 are described below, but the monomer is not limited to these.

Examples of the acrylic acid ester compound as an example of the monomer X4 include methyl acrylate, ethyl acrylate, n-propyl acrylate, isopropyl acrylate, n-butyl acrylate, isobutyl acrylate, t-butyl acrylate, benzyl acrylate, naphthyl acrylate, anthryl acrylate, anthrylmethyl acrylate, phenyl acrylate, glycidyl acrylate, 2,2,2-trifluoroethyl acrylate, cyclohexyl acrylate, isobornyl acrylate, 2-methoxyethyl acrylate, methoxytriethylene glycol acrylate, 2-ethoxyethyl acrylate, tetrahydrofurfuryl acrylate, 3-methoxybutyl acrylate, 2-methyl-2-adamanthyl acrylate, 2-propyl-2-adamanthyl acrylate, 8-methyl-8-tricyclodecyl acrylate, and 8-ethyl-8-tricyclodecyl acrylate.

Examples of the methacrylic acid ester compound as an example of the monomer X4 include methyl methacrylate, ethyl methacrylate, n-propyl methacrylate, isopropyl methacrylate, n-butyl methacrylate, isobutyl methacrylate, t-butyl methacrylate, benzyl methacrylate, naphthyl methacrylate, anthryl methacrylate, anthrylmethyl methacrylate, phenyl methacrylate, glycidyl methacrylate, 2,2,2-trifluoroethyl methacrylate, cyclohexyl methacrylate, isobornyl methacrylate, 2-methoxyethyl methacrylate, methoxy triethylene glycol methacrylate, 2-ethoxy ethyl methacrylate, tetrahydrofurfuryl methacrylate, 3-methoxybutyl methacrylate, 2-methyl-2-adamanthyl methacrylate, γ-butyrolactone methacrylate, 2-propyl-2-adamanthyl methacrylate, 8-methyl-8-tricyclodecyl methacrylate, and 8-ethyl-8-tricyclodecyl methacrylate.

Examples of the vinyl compound as an example of the monomer X4 include methylvinyl ether, benzylvinyl ether, vinyl naphthalene, vinyl carbazole, allyl glycidyl ether, 3-ethenyl-7-oxabicyclo[4.1.0]heptane, 1,2-epoxy-5-hexene, and 1,7-octadiene mono epoxide.

Examples of the styrene compound as an example of the monomer X4 include styrene, methylstyrene, chlorostyrene, and bromostyrene.

Examples of the maleimide compound as an example of the monomer X4 include maleimide, N-methylmaleimide, N-phenylmaleimide, and N-cyclohexylmaleimide.

The proportion of an N-alkoxy alkyl group present in the polymer (the specific copolymer 2) as one example of the component (B) is preferably 40 mol % to 90 mol %, more preferably 50 mol % to 85 mol % per 100 mol of all repeating units of said polymer.

In other words, the amount of the specific monomer X1 used for obtaining the specific copolymer 2 as one example of the component (B) is preferably 40 mol % to 90 mol %, more preferably 50 mol % to 85 mol %, based on the total amount of all monomers used for obtaining the specific copolymer 2 as one example of the component (B).

When the total amount of the specific monomer X1 used is less than 40 mol %, curing caused by thermal cross-linkage with the component (A) may be insufficient. In contrast, when the total amount of the specific monomer X1 used is more than 90 mol %, adhesion to a substrate may be adversely affected.

The proportion of the side chain group, containing the polymerizable C=C double bond, present in the polymer (the specific copolymer 2) as one example of the component (B) is preferably 10 mol % to 60 mol %, more preferably 15 mol % to 50 mol % per 100 mol of all repeating units of said polymer.

In other words, the amount of the specific monomer X3 used for obtaining the specific copolymer 2 as one example of the component (B) is preferably 10 mol % to 60 mol %, more preferably 15 mol % to 50 mol %, based on the total amount of all monomers used for obtaining the specific copolymer 2 as one example of the component (B).

When the total amount of the specific monomer X3 used is less than 10 mol %, adhesion to a liquid crystal layer may be insufficient. In contrast, when the total amount of the specific monomer X3 used is more than 60 mol %, curing caused by thermal cross-linkage with the component (A) may be insufficient.

Although the method for obtaining the specific copolymer 2 as one example of the component (B) is not limited to a particular method, the specific copolymer 2 can be obtained, for example, by subjecting the specific monomer X1, the specific monomer X3, another monomer such as the monomer X4 if desired, and a polymerization initiator or the like to polymerization reaction at a temperature of 50° C. to 110° C. in a solvent in which they coexist. The solvent used herein is not limited as long as the solvent can dissolve the monomers of the respective Formulae X, the other monomer to be used if desired, and the polymerization initiator or the like. Specific examples of the solvent will be recited in <Solvent> below.

The acrylic polymer as an example of the specific copolymer 2 that is obtained by the above-described method is typically in a solution state of being dissolved in the solvent, and, in the present invention, can be used as it is as a solution of the component (B).

A solution of the acrylic polymer as an example of the specific copolymer 2 that is obtained by the above-described method is poured with stirring into diethyl ether, water, or the like to be reprecipitated. The thus-formed precipitate is filtered and washed, and then dried at room temperature or dried by heating, under atmospheric pressure or reduced pressure, whereby a powder of the specific copolymer 2 as one example of the component (B) is prepared. By the above-described operation, the polymerization initiator and an unreacted monomer that coexist with the specific copolymer 2 as one example of the component (B) can be removed, and consequently, a powder of the purified specific copolymer 2 as one example of the component (B) is obtained. In the case where the specific copolymer 2 cannot be sufficiently purified by one operation, the obtained powder may be redissolved in a solvent, followed by repeating the above-described operation.

In the composition of the present invention for forming a cured film on a surface of an optical film, the specific copolymer 2 as one example of the component (B) may be used in the form of powder or in the form of a solution in which the purified powder is redissolved in a solvent described below.

Furthermore, in the composition of the present invention for forming a cured film on a surface of an optical film, the specific copolymer 2 as one example of the component (B) may be a mixture of a plurality of types of copolymers.

The weight-average molecular weight of such polymer is 1,000 to 500,000, preferably 2,000 to 200,000, more preferably 3,000 to 150,000, still more preferably 3,000 to 50,000.

The content of the cross-linking agent as the component (B) in the cured-film formation composition of the present invention is preferably 1 part by mass to 600 parts by mass, more preferably 5 parts by mass to 400 parts by mass, based on 100 parts by mass of the compound as the component (A). When the content of the cross-linking agent is excessively low, the solvent resistance of a cured film obtained from the cured-film formation composition decreases, and the vertical-orientation properties deteriorate. In contrast, when the content is excessively high, the vertical-orientation properties and the preservation stability sometimes deteriorate.

<Component (C)>

The cured-film formation composition of the present invention may contain a polymer having a thermally cross-linkable group as the component (C). The thermally cross-linkable group mentioned herein is, for example, carboxy group, hydroxy group, amino group having active hydrogen, a phenolic hydroxy group, a methylol group, an ester, or an imide.

Examples of the polymer serving as the component (C) include polymers having a linear-chain structure or a branched-chain structure, such as an acrylic polymer, a polyamic acid, a polyimide, a polyvinyl alcohol, a polyester, a polyester polycarboxylic acid, a polyether polyol, a polyester polyol, a polycarbonate polyol, a polycaprolactone polyol, a polyalkylene imine, a polyallylamine, celluloses (a cellulose or derivatives thereof), a phenol novolac resin, and a melamine formaldehyde resin; and cyclic polymers such as cyclodextrins.

Preferable examples of the polymer having a thermally cross-linkable group as the component (C) include an acrylic polymer, hydroxyalkyl cyclodextrins, celluloses, a polyether polyol, a polyester polyol, a polycarbonate polyol, and a polycaprolactone polyol.

The acrylic polymer as a preferred example of the polymer having a thermally cross-linkable group as the component (C) is a polymer obtained by polymerizing a monomer having an unsaturated double bond, such as acrylic acid, methacrylic acid, styrene, or a vinyl compound, the polymer being only required to be obtained by polymerizing monomers containing a monomer having a thermally cross-linkable group, or a mixture thereof. The skeleton of the main chain of the acrylic polymer and the type of the side chain thereof are not limited to particular ones.

Examples of the monomer having a thermally cross-linkable group include a monomer having a polyethylene glycol ester group, a monomer having a $C_{2-5}$ hydroxyalkyl ester group, a monomer having a phenolic hydroxy group, a monomer having a carboxy group, a monomer having an amino group, and a monomer having an alkoxy silyl group and a group of Formula 2 above.

Examples of the above-mentioned monomer having a polyethylene glycol ester group include monoacrylate or monomethacrylate of H—(OCH$_2$CH$_2$)n-OH. The value of n is 2 to 50, preferably 2 to 10.

Examples of the above-mentioned monomer having a $C_{2-5}$ hydroxyalkyl ester group include 2-hydroxyethyl methacrylate, 2-hydroxyethyl acrylate, 2-hydroxypropyl methacrylate, 2-hydroxypropyl acrylate, 4-hydroxybutyl acrylate, and 4-hydroxybutyl methacrylate.

Examples of the above-mentioned monomer having a phenolic hydroxy group include p-hydroxystyrene, m-hydroxystyrene, and o-hydroxystyrene.

Examples of the above-mentioned monomer having a carboxy group mentioned include acrylic acid, methacrylic acid, and vinylbenzoic acid.

Examples of the above-mentioned monomer having an amino group in a side chain include 2-aminoethyl acrylate, 2-aminoethyl methacrylate, aminopropyl acrylate, and aminopropyl methacrylate.

Examples of the above-mentioned monomer having an alkoxy silyl group in a side chain thereof include 3-acryloxypropyl trimethoxy silane, 3-acryloxypropyl triethoxy silane, 3-methacryloxypropyl trimethoxy silane, 3-methacryloxypropyl triethoxy silane, vinyl trimethoxy silane, vinyl triethoxy silane, allyl trimethoxy silane, and allyl triethoxy silane.

Examples of the above-mentioned monomer having a group of Formula 2 above in a side chain thereof include 2-acetoacetoxyethyl acrylate and 2-acetoacetoxyethyl methacrylate.

In the present embodiment, when the acrylic polymer as an example of the component (C) is synthesized, in addition to the above-mentioned monomer, a monomer not having any of a hydroxy group, a carboxy group, an amide group, an amino group, an alkoxy silyl group, and a group of Formula 2 above may be used, as long as not impairing the effects of the present invention.

Specific examples of such monomer include an acrylic acid ester compound, a methacrylic acid ester compound, a maleimide compound, acrylonitrile, maleic anhydride, a styrene compound, and a vinyl compound.

Examples of the acrylic acid ester compound include methyl acrylate, ethyl acrylate, isopropyl acrylate, benzyl acrylate, naphthyl acrylate, anthryl acrylate, anthrylmethyl acrylate, phenyl acrylate, 2,2,2-trifluoroethyl acrylate, tert-butyl acrylate, cyclohexyl acrylate, isobornyl acrylate, 2-methoxyethyl acrylate, methoxytriethylene glycol acrylate, 2-ethoxyethyl acrylate, tetrahydrofurfuryl acrylate, 3-methoxybutyl acrylate, 2-methyl-2-adamanthyl acrylate, 2-propyl-2-adamanthyl acrylate, 8-methyl-8-tricyclodecyl acrylate, and 8-ethyl-8-tricyclodecyl acrylate.

Examples of the methacrylic acid ester compound include methyl methacrylate, ethyl methacrylate, isopropyl methacrylate, benzyl methacrylate, naphthyl methacrylate, anthryl methacrylate, anthrylmethyl methacrylate, phenyl methacrylate, 2,2,2-trifluoroethyl methacrylate, tert-butyl methacrylate, cyclohexyl methacrylate, isobornyl methacrylate, 2-methoxyethyl methacrylate, methoxy triethylene glycol methacrylate, 2-ethoxy ethyl methacrylate, tetrahydrofurfuryl methacrylate, 3-methoxybutyl methacrylate, 2-methyl-2-adamanthyl methacrylate, 2-propyl-2-adamanthyl methacrylate, 8-methyl-8-tricyclodecyl methacrylate, and 8-ethyl-8-tricyclodecyl methacrylate.

Examples of the maleimide compound include maleimide, N-methylmaleimide, N-phenylmaleimide, and N-cyclohexylmaleimide.

Examples of the styrene compound include styrene, methylstyrene, chlorostyrene, and bromostyrene.

Examples of the vinyl compound include vinyl ether, methylvinyl ether, benzylvinyl ether, 2-hydroxyethyl vinyl ether, phenylvinyl ether, and propylvinyl ether.

The usage amount of the monomer having a thermally cross-linkable group that is used for obtaining the acrylic polymer as an example of the component (C) is preferably 2 mol % to 98 mol %, based on the total amount of all monomers used for obtaining the acrylic polymer as an example of the component (C). When the usage amount of the monomer having a thermally cross-linkable group is excessively small, the liquid-crystal orientation properties of an obtained cured film are prone to be insufficient. In contrast, when the usage amount of the monomer is excessively large, compatibility with the component (A) is prone to be lower.

Although the method for obtaining the acrylic polymer as an example of the component (C) is not limited to a particular method, the acrylic polymer can be obtained, for example, by subjecting the monomer having a thermally cross-linkable group, another monomer not having a thermally cross-linkable group if desired, and a polymerization initiator or the like to polymerization reaction at a temperature of 50° C. to 110° C. in a solvent in which they coexist. The solvent used herein is not limited as long as the solvent can dissolve the monomer having a thermally cross-linkable group, the other monomer not having a thermally cross-linkable group that is used if desired, and a polymerization initiator or the like. Specific examples of the solvent will be recited in <Solvent> below.

The acrylic polymer obtained by the above-described method as an example of the component (C) is typically in a solution state of being dissolved in the solvent.

Furthermore, a solution of the acrylic polymer obtained by the above-described method as an example of the component (C) is poured with stirring into diethyl ether, water, or the like to be reprecipitated. The thus-formed precipitate is filtered and washed, and then dried at room temperature or dried by heating, under atmospheric pressure or reduced pressure, whereby a powder of the acrylic polymer as an example of the component (C) is prepared. By the above-described operation, the polymerization initiator and an unreacted monomer that coexist with the acrylic polymer as an example of the component (C) can be removed, and consequently, a powder of the purified acrylic polymer as an example of the component (C) is obtained. In the case where the acrylic polymer cannot be sufficiently purified by one operation, the obtained powder may be redissolved in a solvent, followed by repeating the above-described operation.

The acrylic polymer being a preferred example of the component (C) has a weight-average molecular weight of preferably 3,000 to 200,000, more preferably 4,000 to 150,000, and still more preferably 5,000 to 100,000. An excessively high weight-average molecular weight exceeding 200,000 may reduce the solubility in solvent, so that the handling property may deteriorate, and an excessively low weight-average molecular weight below 3,000 may cause insufficient curing during heat curing, so that the solvent resistance and the heat resistance may decrease. The weight-average molecular weight herein is a value obtained by gel permeation chromatography (GPC) using polystyrene as the standard sample. The same method is used hereinafter in the present specification.

Examples of the polyether polyol being one preferred example of the polymer having a thermally cross-linkable group as the component (C) include those obtained by adding propylene oxide, a polyethylene glycol, or a polypropylene glycol, or the like, to a polyhydric alcohol such as a polyethylene glycol, a polypropylene glycol, propylene glycol, bisphenol A, triethylene glycol, and sorbitol. Specific examples of the polyether polyol include ADEKA polyether P-series, G-series, EDP-series, BPX-series, FC-series, and CM-series manufactured by ADEKA Corporation; and UNIOX (registered trademark) HC-40, HC-60, ST-30E, ST-40E, G-450, and G-750, UNIOL (registered trademark) TG-330, TG-1000, TG-3000, TG-4000, HS-1600D, DA-400, DA-700, and DB-400, and NONION (registered trademark) LT-221, ST-221, and OT-221 manufactured by NOF Corporation.

Examples of the polyester polyol being one preferred example of the polymer having a thermally cross-linkable group as the component (C) include those obtained by causing a polyhydric carboxylic acid such as adipic acid, sebacic acid, and isophthalic acid to react with a diol such as ethylene glycol, propylene glycol, butylene glycol, a polyethylene glycol, and a polypropylene glycol. Specific examples of the polyester polyol include POLYLITE (registered trademark) OD-X-286, OD-X-102, OD-X-355, OD-X-2330, OD-X-240, OD-X-668, OD-X-2108, OD-X-2376, OD-X-2044, OD-X-688, OD-X-2068, OD-X-2547, OD-X-2420, OD-X-2523, OD-X-2555, and OD-X-2560 manufactured by DIC corporation; and Polyol P-510, P-1010, P-2010, P-3010, P-4010, P-5010, P-6010, F-510, F-1010, F-2010, F-3010, P-1011, P-2011, P-2013, P-2030, N-2010, and PNNA-2016 manufactured by Kuraray Co., Ltd.

Examples of the polycaprolactone polyol being one preferred example of polymer having a thermally cross-linkable group as the component (C) include those obtained by causing ring-opening polymerization of s-caprolactone, using a polyhydric alcohol such as trimethylolpropane and ethylene glycol as an initiator. Specific examples of the polycaprolactone polyol include POLYLITE (registered trademark) OD-X-2155, OD-X-640, and OD-X-2568 manufactured by DIC Corporation; and PLACCEL (registered trademark) 205, L205AL, 205U, 208, 210, 212, L212AL, 220, 230, 240, 303, 305, 308, 312, and 320 manufactured by Daicel Chemical Industries, Ltd.

Examples of the polycarbonate polyol being one preferred example of the polymer having a thermally cross-linkable group as the component (C) include those obtained by causing a polyhydric alcohol such as trimethylolpropane and ethylene glycol to react with diethyl carbonate, diphenyl carbonate, ethylene carbonate, or the like. Specific examples of the polycarbonate polyol include PLACCEL (registered trademark) CD205, CD205PL, CD210, and CD220 manufactured by Daicel Chemical Industries, Ltd; and C-590, C-1050, C-2050, C-2090, and C-3090 manufactured by Kuraray Co., Ltd.

Examples of the celluloses being one preferred example of the polymer having a thermally cross-linkable group as the component (C) include hydroxyalkyl celluloses such as hydroxyethyl cellulose and hydroxypropyl cellulose; hydroxyalkyl alkyl celluloses such as hydroxyethyl methyl cellulose, hydroxypropyl methyl cellulose, and hydroxyethyl ethyl cellulose; and celluloses. For example, the hydroxyalkyl celluloses such as hydroxyethyl cellulose and hydroxypropyl cellulose are preferred.

Examples of the cyclodextrins being one preferred example of the polymer having a thermally cross-linkable group as the component (C) include cyclodextrins such as α-cyclodextrin, β-cyclodextrin, and γ-cyclodextrin; methylated cyclodextrins such as methyl-α-cyclodextrin, methyl-β-cyclodextrin, and methyl-γ-cyclodextrin; and hydroxyalkyl cyclodextrins such as hydroxymethyl-α-cyclodextrin, hydroxymethyl-β-cyclodextrin, hydroxymethyl-γ-cyclodextrin, 2-hydroxyethyl-α-cyclodextrin, 2-hydroxyethyl-β-cyclodextrin, 2-hydroxyethyl-γ-cyclodextrin, 2-hydroxypropyl-α-cyclodextrin, 2-hydroxypropyl-β-cyclodextrin, 2-hydroxypropyl-γ-cyclodextrin, 3-hydroxypropyl-α-cyclodextrin, 3-hydroxypropyl-β-cyclodextrin, 3-hydroxypropyl-γ-cyclodextrin, 2,3-dihydroxypropyl-α-cyclodextrin, 2,3-dihydroxypropyl-β-cyclodextrin, and 2,3-dihydroxypropyl-γ-cyclodextrin.

Examples of the melamine formaldehyde resin being one preferred example of the polymer having a thermally cross-linkable group as the component (C) is a resin that is obtained by polycondensation between melamine and formaldehyde, and is a resin of the following Formula.

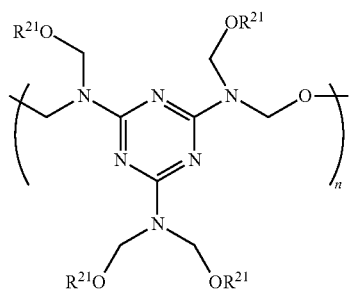

In the Formula, $R^{21}$ is a hydrogen atom or a $C_{1-4}$ alkyl group; and n is a natural number representing the number of repeating units.

In the melamine formaldehyde resin being one preferred example of the component (C), methylol group generated in the polycondensation between melamine and formaldehyde is preferably O-alkylated from the viewpoint of preservation stability.

Although the method for obtaining the melamine formaldehyde resin being one preferred example of the component (C) is not limited to a particular method, the melamine formaldehyde resin is synthesized generally by mixing melamine and formaldehyde, making this mixture weakly alkaline with sodium carbonate, ammonia, or the like, and then heating the mixture at 60° C. to 100° C. By additional reaction with alcohol, the methylol group can be alkoxylated.

The melamine formaldehyde resin being one preferred example of the component (C) has a weight-average molecular weight of preferably 250 to 5,000, more preferably 300 to 4,000, and further preferably 350 to 3,500. An excessively high weight-average molecular weight exceeding 5,000 may reduce the solubility in solvent, so that the handling property may deteriorate, and an excessively low weight-average molecular weight below 250 may cause insufficient curing during heat curing, so that the effect of improving the solvent resistance and the heat resistance cannot be sufficiently obtained in some cases.

In the embodiment of the present invention, the melamine formaldehyde resin being one preferred example of the component (C) may be used in a form of liquid or in a form of solution in which the purified liquid is redissolved in a solvent described below.

Examples of the phenol novolac resin being one preferred example of the polymer having a thermally cross-linkable group as the component (C) include a phenol-formaldehyde polycondensate.

In the cured-film formation composition of the present embodiment, the polymer having a thermally cross-linkable group as the component (C) may be used in the form of powder or in the form of a solution in which the purified powder is redissolved in a solvent described below.

The content of the component (C) in the cured-film formation composition of the present invention is preferably not more than 400 parts by mass, more preferably 10 parts by mass to 380 parts by mass, and still more preferably 40 parts by mass to 360 parts by mass, based on 100 parts by mass of the total amount of the compound as the component (A) and the cross-linking agent as the component (B). When the content of the component (C) is excessively high, liquid-crystal orientation properties are prone to be lower. In contrast, when the content of the component (C) is excessively low, adhesive properties are prone to be lower.

Furthermore, in the cured-film formation composition of the present embodiment, the component (C) may be a mixture of a plurality of types of the polymers exemplified as the component (C).

<Component (D)>

In addition to the above-mentioned component (A) and component (B), the cured-film formation composition of the present invention may further contain a cross-linking catalyst as a component (D).

For the cross-linking catalyst serving as the component (D), for example, an acid or a thermal acid generator may be suitably used. This component (D) is effective in promoting the heat-curing reaction of the cured-film formation composition of the present invention.

Specific examples of the component (D) include a sulfonic acid group-containing compound, hydrochloric acid, and salts thereof, as the above-mentioned acid. The above-mentioned thermal acid generator is not limited to a particular one as long as the thermal acid generator is a compound that thermally decomposes to generate an acid during heating treatment, that is, a compound that thermally decomposes to generate an acid at a temperature of 80° C. to 250° C.

Specific examples of the above-mentioned acid include hydrochloric acid and salts thereof; and sulfonic acid group-containing compounds, such as methanesulfonic acid, ethanesulfonic acid, propanesulfonic acid, butanesulfonic acid, pentanesulfonic acid, octanesulfonic acid, benzenesulfonic acid, p-toluenesulfonic acid, camphorsulfonic acid, trifluoromethanesulfonic acid, p-phenolsulfonic acid, 2-naphthalenesulfonic acid, mesitylenesulfonic acid, p-xylene-2-sulfonic acid, m-xylene-2-sulfonic acid, 4-ethylbenzenesulfonic acid, 1H,1H,2H,2H-perfluorooctanesulfonic acid, perfluoro(2-ethoxyethane)sulfonic acid, pentafluoroethanesulfonic acid, nonafluorobutane-1-sulfonic acid, and dodecylbenzenesulfonic acid, and hydrates and salts thereof.

Examples of the compound that generates an acid by heat include bis(tosyloxy)ethane, bis(tosyloxy)propane, bis(tosyloxy)butane, p-nitrobenzyl tosylate, o-nitrobenzyl tosylate, 1,2,3-phenylene tris(methylsulfonate), p-toluenesulfonic acid pyridinium salt, p-toluenesulfonic acid morphonium salt, p-toluenesulfonic acid ethyl ester, p-toluenesulfonic acid propyl ester, p-toluenesulfonic acid butyl ester, p-toluenesulfonic acid isobutyl ester, p-toluenesulfonic acid methyl ester, p-toluenesulfonic acid phenethyl ester, cyanomethyl p-toluenesulfonate, 2,2,2-trifluoroethyl p-toluenesulfonate, 2-hydroxybutyl p-toluenesulfonate, N-ethyl-p-toluenesulfonamide, and compounds of the following formulae.

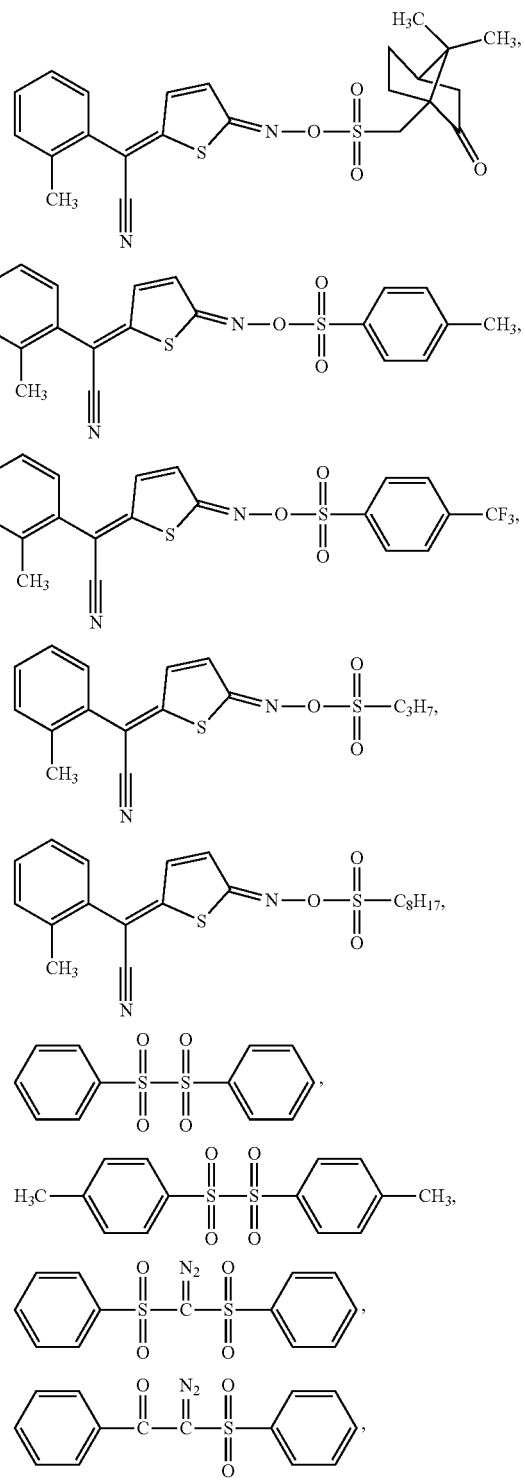

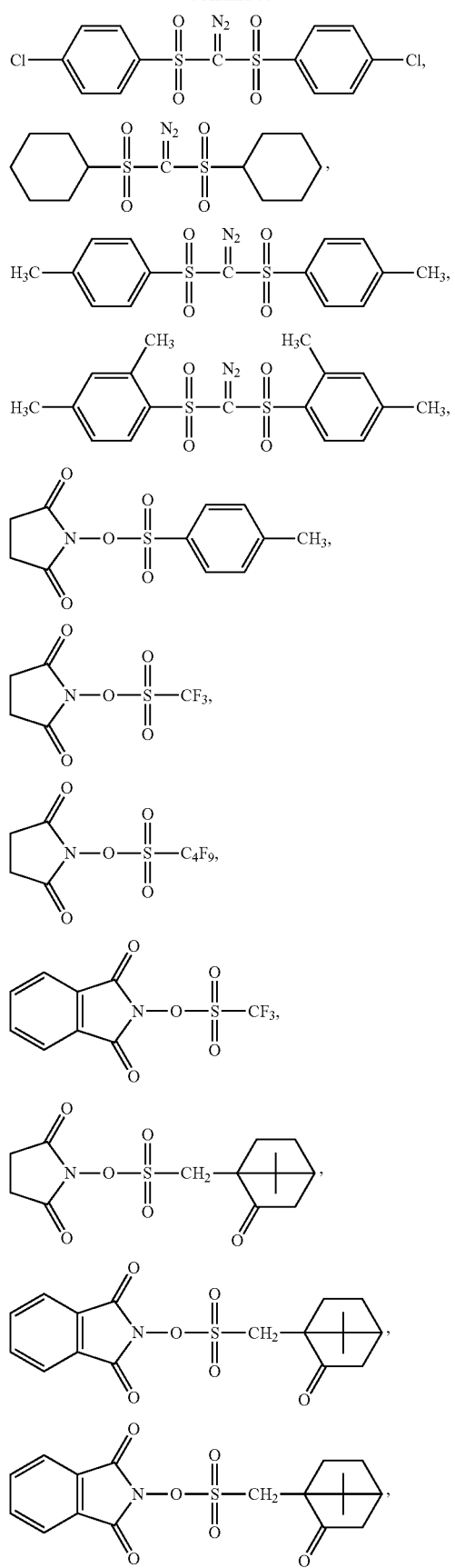
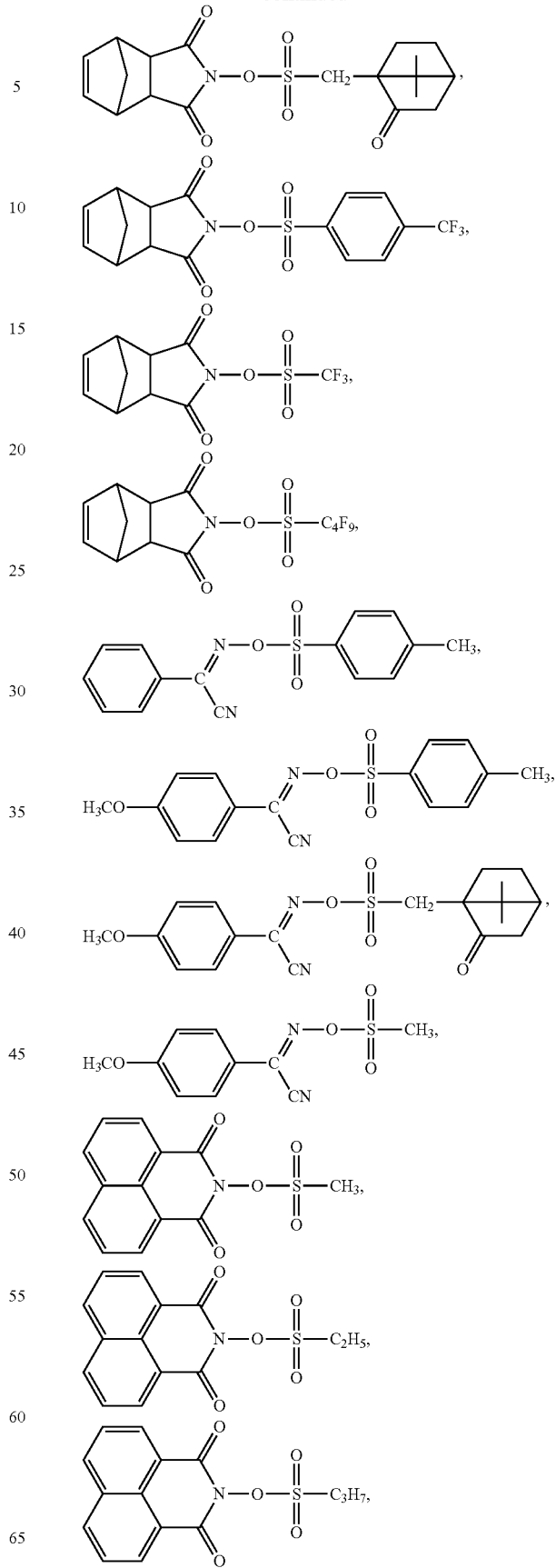

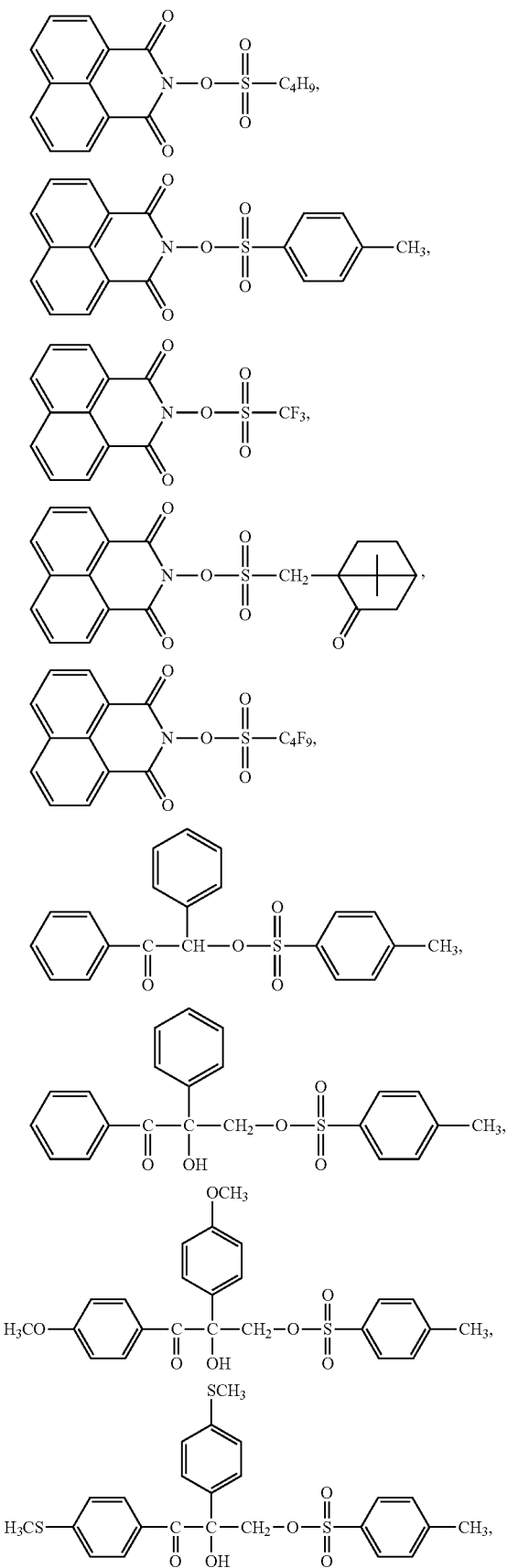

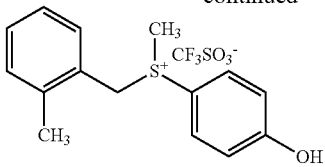

The content of the component (D) in the cured-film formation composition of the present invention is preferably 0.01 part by mass to 20 parts by mass, more preferably 0.1 part by mass to 15 parts by mass, still more preferably 0.5 part by mass to 10 parts by mass, based on 100 parts by mass of the total amount of the compound as the component (A) and the cross-linking agent as the component (B). When the content of the component (D) is not less than 0.01 part by mass, sufficient heat-curing properties and sufficient solvent resistance can be imparted to the cured-film formation composition. However, when the component (D) content is more than 20 parts by mass, the preservation stability of the composition may be reduced.

<Component (E)>

The cured-film formation composition of the present invention may further contain, as a component (E), a component that enhances the adhesive properties of a cured film formed (an adhesion enhancing component).

When a cured film formed from the cured-film formation composition of the present embodiment that contains the component (E) is used as an orientation material, a polymerizable functional group of a polymerizable liquid crystal and a cross-linking reactive moiety of an orientation material can be linked by covalent bonding so as to enhance the adhesion between the orientation material and the layer of the polymerizable liquid crystal. Consequently, the retardation material of the present embodiment that is formed by laminating the cured polymerizable liquid crystal on the orientation material of the present embodiment can retain excellent adhesive properties even under high-temperature and high-humidity conditions, and accordingly, can exhibit high durability against peeling or the like.

As the component (E), a compound having a polymerizable group and a group selected from hydroxy group and an N-alkoxymethyl group is preferable.

Examples of such component (E) include a compound having hydroxy group and (meth)acrylic group, a compound having an N-alkoxymethyl group and (meth)acrylic group, and a polymer having an N-alkoxymethyl group and (meth)acrylic group. Specific examples of these are recited below.

Examples of the component (E) include a polyfunctional acrylate containing hydroxy group (hereinafter, also referred to as a hydroxy group-containing polyfunctional acrylate).

Examples of the hydroxy group-containing polyfunctional acrylate as an example of the component (E) include pentaerythritol triacrylate and dipentaerythritol pentaacrylate.

Other examples of the component (E) include a compound having one acrylic group and at least one hydroxy group. Preferred examples of the compound having one acrylic group and at least one hydroxy group are mentioned below. It should be noted that the compound as the component (E) is not limited to the following compound examples.

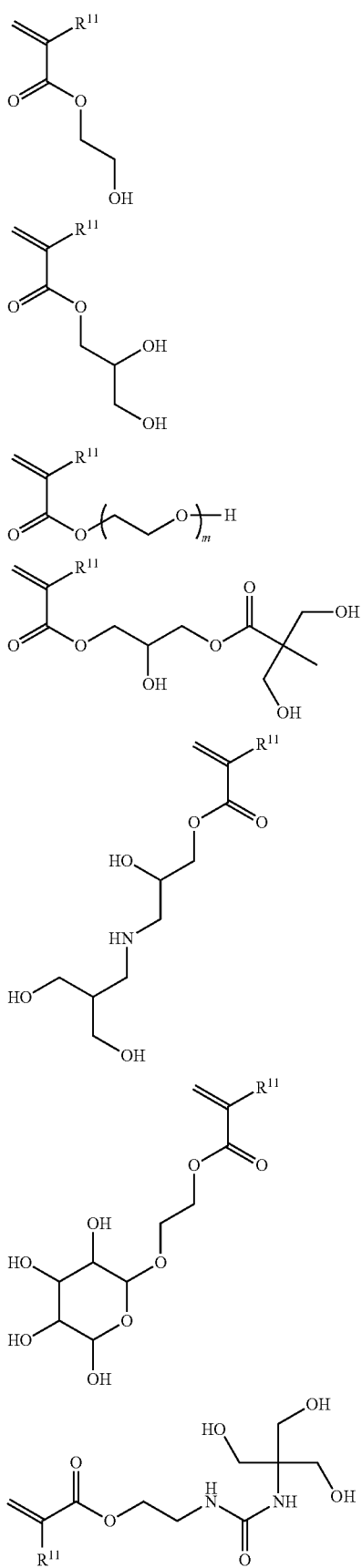

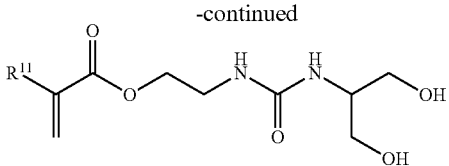

(In the formula, $R^{11}$ is a hydrogen atom or methyl group; and m is an integer of 1 to 10.)

Furthermore, another example of the component (E) includes a compound having at least one group containing a polymerizable C=C double bond in one molecule and at least one N-alkoxymethyl group.

Examples of the group containing a polymerizable C=C double bond include acrylic group, methacrylic group, vinyl group, allyl group, and maleimide group.

Examples of a nitrogen atom N of the N-alkoxymethyl group include a nitrogen atom of amide, a nitrogen atom of thioamide, a nitrogen atom of urea, a nitrogen atom of thiourea, a nitrogen atom of urethane, and a nitrogen atom bonded to a vicinal position of a nitrogen atom of a nitrogen-containing hetero ring. Accordingly, examples of the N-alkoxymethyl group include a group having a structure in which an alkoxymethyl group is bonded to a nitrogen atom selected from a nitrogen atom of amide, a nitrogen atom of thioamide, a nitrogen atom of urea, a nitrogen atom of thiourea, a nitrogen atom of urethane, and a nitrogen atom bonded to a vicinal position of a nitrogen atom of a nitrogen-containing hetero ring.

As the component (E), the compound is only required to have any of the above-mentioned groups, and preferred examples of the compound include a compound of Formula (X1) above.

Preferred examples of another aspect of the compound having a group containing a polymerizable C=C double bond and an N-alkoxymethyl group as the component (E) include a compound of Formula (X2) below.

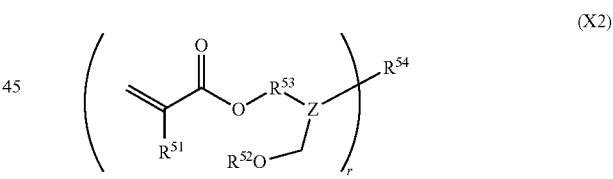

In the Formula, $R^{51}$ is a hydrogen atom or methyl group.

$R^{52}$ is a $C_{2-20}$ alkyl group, a $C_{5-6}$ monovalent aliphatic-ring group, or a $C_{5-6}$ aliphatic ring-containing monovalent aliphatic group, and the structure thereof may include an ether bond.

$R^{53}$ is a linear or branched $C_{2-20}$ alkylene group, a $C_{5-6}$ divalent aliphatic-ring group, or a $C_{5-6}$ aliphatic ring-containing divalent aliphatic group, and the structure thereof may include an ether bond.

$R^{54}$ is a linear or branched $C_{1-20}$ aliphatic group with a valence of two to nine, a $C_{5-6}$ aliphatic-ring group with a valence of two to nine, or a $C_{5-6}$ aliphatic ring-containing aliphatic group with a valence of two to nine, and one methylene group or a plurality of unadjacent methylene groups each may be replaced with an ether bond.

Z is >NCOO— or —OCON< (herein, "—" indicates that the number of bonding hands is one. ">" and "<" indicate that the number of bonding hands is two and an alkoxymethyl group (i.e., —OR$^{52}$ group) binds to either of the two bonding hands.).

"r" is a natural number of two to nine.

Specific examples of the C$_{2-20}$ alkylene group in the definition of R$^{53}$ include a divalent group obtained by further removing one hydrogen atom from a C$_{2-20}$ alkyl group.

Specific examples of the C$_{1-20}$ aliphatic group with a valence of two to nine in the definition of R$^{54}$ include a group with a valence of two to nine obtained by further removing one to eight hydrogen atoms from a C$_{1-20}$ alkyl group.

The C$_1$ alkyl group is methyl group, and specific examples of the C$_{2-20}$ alkyl group include ethyl group, n-propyl group, i-propyl group, n-butyl group, i-butyl group, s-butyl group, t-butyl group, n-pentyl group, 1-methyl-n-butyl group, 2-methyl-n-butyl group, 3-methyl-n-butyl group, 1,1-dimethyl-n-propyl group, n-hexyl group, 1-methyl-n-pentyl group, 2-methyl-n-pentyl group, 1,1-dimethyl-n-butyl group, 1-ethyl-n-butyl group, 1,1,2-trimethyl-n-propyl group, n-heptyl group, n-octyl group, n-nonyl group, n-decyl group, n-undecyl group, n-dodecyl group, n-tridecyl group, n-tetradecyl group, n-pentadecyl group, n-hexadecyl group, n-heptadecyl group, n-octadecyl group, n-nonadecyl group, n-eicosyl group, cyclopentyl group, cyclohexyl group, groups in which one or more out of these groups are bonded within a range of up to C$_{20}$, and groups in which one methylene or a plurality of unadjacent methylene groups each are replaced with an ether bond.

Among them, a C$_{2-10}$ alkylene group is preferred, and it is particularly preferable that R$^{53}$ be ethylene group and R$^{54}$ be hexylene group from the viewpoint of availability of raw material, for example.

Specific examples of the C$_{1-20}$ alkyl group in the definition of R$^{52}$ include the specific examples of the C$_{2-20}$ alkyl group in the definition of R$^{53}$ and methyl group. Among them, the C$_{1-6}$ alkyl group is preferred, and the methyl group, the ethyl group, the n-propyl group, and the n-butyl group are particularly preferred.

Examples of r include natural numbers of two to nine, and among them, two to six are preferred.

The compound (X2) is obtained by a production method illustrated in a reaction scheme below. Specifically, the compound (X2) is produced by subjecting a carbamate compound (hereinafter, also called "compound (X2-1)") of Formula (X2-1) below having acrylic group or methacrylic group to reaction in a solvent into which trimethylsilyl chloride and paraformaldehyde are added to synthesize an intermediate of Formula (X2-2) below, and adding alcohol of R$^{52}$—OH to this reaction solution thereby causing the solution to react.

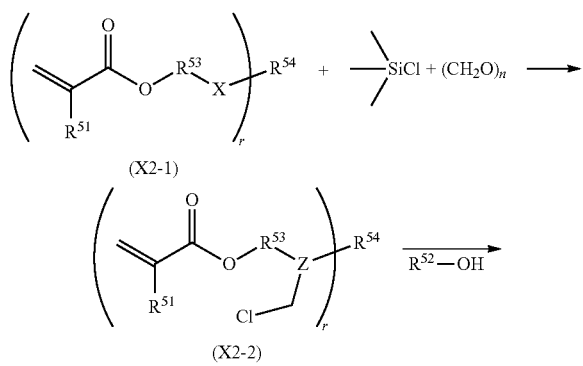

(X2-1)

(X2-2)

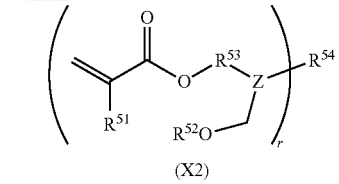

(X2)

In the Formulae, R$^{51}$, R$^{52}$, R$^{53}$, R$^{54}$, Z, and r are those described above; and X is —NHCOO— or —OCONH—.

Although the used amount of trimethylsilyl chloride and paraformaldehyde to the compound (X2-1) is not limited to a particular amount, in order to complete the reaction, with respect to one carbamate bond in a molecule, 1.0 equivalent to 6.0 equivalents of trimethylsilyl chloride is/are preferably used, and 1.0 equivalent to 3.0 equivalents of paraformaldehyde is/are preferably used, in which the used equivalents of trimethylsilyl chloride are preferably larger than the used equivalents of paraformaldehyde.

The reaction solvent is not limited as long as the solvent is inert to reaction, and examples thereof include hydrocarbons such as hexane, cyclohexane, benzene, and toluene; halogenated hydrocarbons such as methylene chloride, carbon tetrachloride, chloroform, and 1,2-dichloroethane; ethers such as diethyl ether, diisopropyl ether, 1,4-dioxane, and tetrahydrofuran; nitriles such as acetonitrile and propionitrile; a nitrogen-containing aprotic polar solvent such as N,N-dimethylformamide, N,N-dimethylacetamide, N-methyl-2-pyrrolidone, and 1,3-dimethyl-2-imidazolidinone; and pyridines such as pyridine and a picoline. These solvents may be used singly or in combination of two or more types. Methylene chloride and chloroform are preferred, and methylene chloride is more preferred.

Although the used amount (the reaction concentration) of the solvent is not limited to a particular value, the reaction may be performed without the solvent, or the solvent may be used in an amount of 0.1 time to 100 times by mass the amount of the compound (X2-1). The amount used is preferably 1 time to 30 times by mass, and more preferably 2 times to 20 times by mass.

Although the reaction temperature is not limited to a particular temperature, the reaction temperature is −90° C. to 200° C., preferably −20° C. to 100° C., and more preferably −10° C. to 50° C.

The reaction time is generally 0.05 hour to 200 hours, and preferably 0.5 hour to 100 hours.

The reaction can be performed under atmospheric pressure or increased pressure, and may be performed in a batch process or in a continuous process.

When the reaction is performed, a polymerization inhibitor may be added. As the polymerization inhibitor, BHT (2,6-di-tert-butyl-para-cresol), hydroquinone, paramethoxyphenol, or the like can be used, and any agent that inhibits polymerization of acrylic group or methacrylic group may be used without being limited.

Although the addition amount of the polymerization inhibitor added is not limited to a particular value, the addition amount is preferably 0.0001 wt % to 10 wt %, and preferably 0.01 wt % to 1 wt % with respect to total used amount (mass) of the compound (X2-1). In the present specification, wt % means % by mass.

In the process of causing the intermediate (X2-2) to react with alcohol, a base may be added in order to prevent hydrolysis under acidic conditions. Examples of the base include pyridines such as pyridine and a picoline; and tertiary amines such as trimethylamine, triethylamine, diisopropylethylamine, and tributylamine. Triethylamine and diisopropylethylamine are preferred, and triethylamine is more preferred. Although the addition amount of the base added is not limited to a particular value, the addition amount is preferably 0.01 equivalent to 2.0 equivalents, and more preferably 0.5 equivalent to 1.0 equivalent with respect to the addition amount of the trimethylsilyl chloride used during the reaction.

After the intermediate (X2-2) is obtained from the compound (X2-1), without isolating the intermediate (X2-2), alcohol may be added thereto for reaction.

Although the method for synthesizing the compound (X2-1) is not limited to a particular method, the compound (X2-1) can be produced by causing a (meth)acryloyloxyalkyl isocyanate to react with a polyol compound, or causing a hydroxyalkyl (meth)acrylate compound to react with a polyisocyanate compound.

Specific examples of the (meth)acryloyloxyalkyl isocyanate include 2-methacryloyloxyethyl isocyanate (trade name: Karenz MOI [registered trademark] manufactured by Showa Denko K.K.) and 2-acryloyloxyethyl isocyanate (trade name: Karenz AOI [registered trademark] manufactured by Showa Denko K.K.).

Specific examples of the polyol compound include a diol compound such as ethylene glycol, propylene glycol, 1,4-butanediol, 1,3-butanediol, 1,5-pentanediol, neopentylglycol, 3-methyl-1,5-pentanediol, 1,6-hexanediol, and 1,4-cyclohexane dimethanol; a triol compound such as glycerin and trimethylolpropane; pentaerythritol; dipentaerythritol; and diglycerine.

Specific examples of the hydroxyalkyl (meth)acrylate compound include a monomer having a hydroxy group such as 2-hydroxyethyl acrylate, 2-hydroxyethyl methacrylate, 2-hydroxypropyl acrylate, 2-hydroxypropyl methacrylate, 4-hydroxybutyl acrylate, 4-hydroxybutyl methacrylate, diethylene glycol monoacrylate, diethylene glycol monomethacrylate, a poly(ethylene glycol)ethylether acrylate, and a poly(ethylene glycol)ethylether methacrylate.

Specific examples of the polyisocyanate compound include aliphatic diisocyanates such as hexamethylene diisocyanate, 2,4,4-trimethyl hexamethylene diisocyanate, and dimer acid diisocyanate; alicyclic diisocyanates such as isophorone diisocyanate, 4,4'-methylene bis(cyclohexyl isocyanate) and ω,ω'-diisocyanate dimethylcyclohexane; triisocyanates such as lysine ester triisocyanate, 1,6,11-undecane triisocyanate, 1,8-diisocyanate-4-isocyanate methyloctane, 1,3,6-hexamethylene triisocyanate, and bicycloheptane triisocyanate.

These (meth)acryloyloxyalkyl isocyanate compounds, polyol compounds, hydroxyalkyl (meth)acrylate compounds, and polyisocyanate compounds are generally commercially available, and can also be synthesized by known methods.

The content of the component (E) in the cured-film formation composition of the present embodiment is preferably 0.1 part by mass to 100 parts by mass, more preferably 5 parts by mass to 70 parts by mass, based on 100 parts by mass of the total amount of the compound as the component (A) and the cross-linking agent as the component (B). When the content of the component (E) is not less than 0.1 part by mass, sufficient adhesive properties can be imparted to a cured film formed. However, when the content of the component (E) is more than 100 parts by mass, liquid-crystal orientation properties are prone to be lower.

Furthermore, in the cured-film formation composition of the present embodiment, the component (E) may be a mixture of a plurality of types of the compounds exemplified as the component (E).

<Solvent>

The cured-film formation composition of the present invention is used mainly in a solution state in which the composition is dissolved in a solvent. The type, structure, and the like of the solvent used herein are not limited as long as the solvent can dissolve the component (A), the component (B), and, if necessary, the component (C), the component (D), the component (E), and/or other additives described below.

Specific examples of the solvent include methanol, ethanol, n-propanol, isopropanol, n-butanol, isobutanol, 2-methyl-1-butanol, n-pentanol, ethylene glycol monomethyl ether, ethylene glycol monoethyl ether, methyl cellosolve acetate, ethyl cellosolve acetate, diethylene glycol, diethylene glycol monomethyl ether, diethylene glycol monoethyl ether, propylene glycol, propylene glycol monomethyl ether, propylene glycol monomethyl ether acetate, propylene glycol monoethyl ether, propylene glycol propyl ether, propylene glycol propyl ether acetate, toluene, xylene, methyl ethyl ketone, isobutyl methyl ketone, cyclopentanone, cyclohexanone, 2-butanone, 3-methyl-2-pentanone, 2-pentanone, 2-heptanone, γ-butyrolactone, ethyl 2-hydroxypropionate, ethyl 2-hydroxy-2-methylpropionate, ethyl ethoxyacetate, ethyl hydroxyacetate, methyl 2-hydroxy-3-methylbutanoate, methyl 3-methoxypropinoate, ethyl 3-methoxypropionate, methyl 3-ethoxypropionate, ethyl 3-ethoxypropionate, methyl pyruvate, ethyl pyruvate, ethyl acetate, butyl acetate, ethyl lactate, butyl lactate, cyclopentyl methyl ether, N,N-dimethylformamide, N,N-dimethylacetamide, and N-methyl-2-pyrrolidone.

When a cured film is formed on a resin film by using the cured-film formation composition of the present invention to produce an orientation material, methanol, ethanol, n-propanol, isopropanol, n-butanol, 2-methyl-1-butanol, 2-heptanone, isobutyl methyl ketone, diethylene glycol, propylene glycol, propylene glycol monomethyl ether, propylene glycol monomethyl ether acetate, or the like is preferably employed because the resin film exhibits resistance against these solvents.

These solvents may be used alone, or two or more of them may be used in combination.

<Other Additives>

As long as not impairing the effects of the present invention, the cured-film formation composition of the present invention may further contain, for example, a sensitizer, an adhesion enhancer, a silane coupling agent, a surfactant, a rheology adjusting agent, a pigment, a dye, a preservation stabilizer, an antifoamer, and an antioxidant as other additives, if necessary.

For example, the sensitizer is effective in promoting a photoreaction after a heat-cured film is formed using the resin composition for forming the retardation material of the present invention.

Examples of the sensitizer as one example of the other additives include benzophenone, anthracene, anthraquinone, thioxanthone, and derivatives thereof, and nitrophenyl compounds. Among them, benzophenone derivatives and nitrophenyl compounds are preferred. Specific examples of the preferred compounds include N,N-diethylaminobenzophenone, 2-nitrofluorene, 2-nitrofluorenone, 5-nitroacenaphthene, 4-nitrobiphenyl, 4-nitrocinnamic acid, 4-nitrostilbene, 4-nitrobenzophenone, and 5-nitroindole. In particular, N,N-diethylaminobenzophenone, which is a derivative of benzophenone, is preferred.

The sensitizers are not limited to those mentioned above. The sensitizers may be used alone or in combination of two or more types of the compounds.

The proportion of the sensitizer used in the resin composition for forming the retardation material of the present invention is preferably from 0.1 part by mass to 20 parts by mass, more preferably from 0.2 part by mass to 10 parts by mass, based on 100 parts by mass of the total amount of the component (A) to the component (E). When this proportion is excessively low, the effects of the sensitizer may be insufficiently obtained. In contrast, when the proportion is excessively high, a decrease in the transmittance and roughening of coating may occur.

<Preparation of Cured-Film Formation Composition>

The cured-film formation composition of the present invention is a composition that contains a compound as the component (A) and a cross-linking agent as the component (B), and, if necessary, may further contain a polymer having a thermally cross-linkable group as the component (C), a cross-linking catalyst as the component (D), and an adhesion enhancing component as the component (E), and may further contain other additives unless the effects of the present invention are impaired. The cured-film formation composition is used typically in a solution state in which these components are dissolved in a solvent.

Preferred examples of the cured-film formation composition of the present invention are listed below.

[1]: A cured-film formation composition that contains: the component (A); 1 part by mass to 300 parts by mass of the component (B), based on 100 parts by mass of the component (A); and 1 part by mass to 400 parts by mass of the component (C), based on 100 parts by mass of the total amount of the compound as the component (A) and the cross-linking agent as the component (B).

[2]: A cured-film formation composition that contains: the component (A); 1 part by mass to 600 parts by mass of the component (B), based on 100 parts by mass of the component (A); 1 part by mass to 400 parts by mass of the component (C), based on 100 parts by mass of the total amount of the compound as the component (A) and the cross-linking agent as the component (B); and a solvent.

[3]: A cured-film formation composition that contains: the component (A); 1 part by mass to 600 parts by mass of the component (B), based on 100 parts by mass of the component (A); 1 part by mass to 400 parts by mass of the component (C), based on 100 parts by mass of the total amount of the compound as the component (A) and the cross-linking agent as the component (B); 0.01 part by mass to 20 parts by mass of the component (D), based on 100 parts by mass of the total amount of the compound as the component (A) and the cross-linking agent as the component (B); and a solvent.

[4]: A cured-film formation composition that contains: the component (A); 1 part by mass to 600 parts by mass of the component (B), based on 100 parts by mass of the component (A); 1 part by mass to 400 parts by mass of the component (C), based on 100 parts by mass of the total amount of the compound as the component (A) and the cross-linking agent as the component (B); 0.01 part by mass to 20 parts by mass of the component (D), based on 100 parts by mass of the total amount of the compound as the component (A) and the cross-linking agent as the component (B); 0.1 part by mass to 100 parts by mass of the component (E), based on 100 parts by mass of the total amount of the compound as the component (A) and the cross-linking agent as the component (B); and a solvent.

A blending proportion, a preparation method, and the like in the case of using the cured-film formation composition of the present invention as a solution will be described below in detail.

The proportion of solid content in the cured-film formation composition of the present invention is 1% by mass to 60% by mass, preferably 2% by mass to 50% by mass, more preferably 2% by mass to 20% by mass, but is not limited to these as long as each component is uniformly dissolved in the solvent. The solid content herein is a component remaining after removing the solvent from all the components of the cured-film formation composition.

The method for preparing the cured-film formation composition of the present invention is not limited to a particular method. Examples of the preparation method include: a method in which the component (B), and if necessary, the component (C), the component (D), the component (E), and others are mixed at a predetermined proportion in a solution of the component (A) dissolved in the solvent component, and the resulting mixed solution is made uniform; and a method in which, at an appropriate stage of the above-described preparation method, other additives are further added and mixed in, if necessary.

In the preparation of the cured-film formation composition of the present invention, a solution of the specific copolymer (polymer) obtained by copolymerization reaction in the solvent can be used without being processed. In this case, for example, the component (B), and furthermore, if necessary, the component (C), the component (D), the component (E), and others are mixed in a solution of the component (A) in the same manner as described above to make the resulting mixed solution uniform. At this time, a solvent may be further added for the purpose of adjusting a concentration. Here, the solvent used in the process of preparing the component (A) may be the same as or different from the solvent used for adjusting the concentration of the cured-film formation composition.

The solution of the cured-film formation composition thus prepared is preferably used after being filtered, for example, with a filter having a pore diameter of about 0.2 µm.

<Cured Film, Orientation Material, and Retardation Material>

A cured film can be formed in such a manner that the solution of the cured-film formation composition of the present invention is applied onto a substrate (for example, a silicon/silicon dioxide coated substrate, a silicon nitride substrate, a substrate coated with a metal such as aluminum, molybdenum, or chromium, a glass substrate, a quartz substrate, or an ITO substrate) or onto a film substrate (for example, a resin film such as a triacetylcellulose (TAC) film, a polycarbonate (PC) film, a cycloolefin polymer (COP) film, a cycloolefin copolymer (COC) film, a polyethylene terephthalate (PET) film, an acrylic film, or a polyethylene film) by bar coating, rotation coating, flow coating, roll coating, slit coating, slit coating followed by rotation coating, inkjet coating, printing, or the like, whereby a coating is formed, and then the resulting coating is heated and dried, for example, on a hot plate or in an oven. The cured film is applicable as it is as an orientation material.

As a condition for the heating and drying, it is only required that a cross-linking reaction caused by a cross-linking agent proceeds to such an extent that the component of the cured film (orientation material) is not eluted into a polymerizable liquid crystal solution applied on the cured film. For example, a heating temperature and a heating time that are appropriately selected from a temperature range of 60° C. to 200° C. and a time range of 0.4 minute to 60 minutes are adopted. The heating temperature is preferably 70° C. to 160° C., and the heating time is 0.5 minute to 10 minutes.

The film thickness of the cured film (the orientation material) formed using the cured-film formation composition of the present invention is, for example, 0.05 μm to 5 μm, which can be appropriately selected in consideration of the level differences and optical and electrical properties of a substrate to be used.

The orientation material formed from the cured-film formation composition of the present invention has solvent resistance and heat resistance, and therefore, onto this orientation material, a retardation substance such as a polymerizable liquid crystal solution that has vertical-orientation properties can be applied and oriented on the orientation material. Then, by curing the retardation substance in the oriented state without processing, a retardation material can be formed as a layer having optical anisotropy. In the case where a substrate on which the orientation material is formed is a film, the film is useful as a retardation film.

Alternatively, two substrates thus formed, each having the orientation material of the present invention thereon, are stuck together with a spacer interposed therebetween so that the orientation materials on the respective substrates face each other. Then, a liquid crystal is injected between the substrates, whereby a liquid crystal display element in which the liquid crystal is oriented can be produced.

Thus, the cured-film formation composition of the present invention can be suitably used for producing various retardation materials (retardation films), liquid crystal display elements, and the like.

EXAMPLES

Hereinafter, the present invention will be described in further detail with reference to Examples, but the present invention is not limited to these Examples.

[Abbreviations Used in Examples]

Abbreviations used in examples below mean as follows.

<Raw Materials of Components> jER-828: bisphenol A epoxy resin, manufactured by Mitsubishi Chemical Corporation, molecular weight: 370 jER-1001: bisphenol A epoxy resin, manufactured by Mitsubishi Chemical Corporation, molecular weight: 900

TEPIC-L: trifunctional epoxy compound, manufactured by Nissan Chemical Industries, Ltd.

MCA: p-methoxycinnamic acid

PCA: p-propoxycinnamic acid

MeCA: p-methylcinnamic acid

FCA: p-fluorocinnamic acid

CA: cinnamic acid

BMAA: N-butoxymethyl acrylamide

BTEAC: benzyl triethyl ammonium chloride

AIBN: α,α'-azobisisobutyronitrile

HEMA: 2-hydroxyethyl methacrylate

MMA: methyl methacrylate

<Component (B)>

HMM: melamine cross-linking agent of the following structural formula [CYMEL (registered trademark) 303 (manufactured by Mitsui-Cytec Ltd.)]

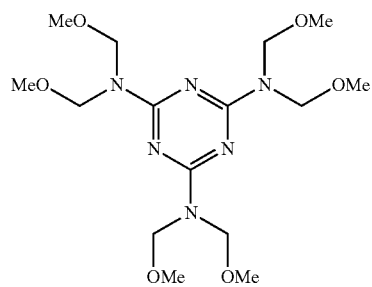 [SMILES: COCN(COC)c1nc(N(COC)COC)nc(N(COC)COC)n1]

<Component (D)>

PTSA: p-toluenesulfonic acid monohydrate

<Solvent>

PM: propylene glycol monomethyl ether

The number-average molecular weight and weight-average molecular weight of the acrylic copolymers obtained in accordance with Synthesis Examples below were measured with a GPC apparatus manufactured by JASCO Corporation (Shodex (registered trademark) column KF 803L and KF 804L) under the condition of performing elution by flowing an elution solvent of tetrahydrofuran, in the columns (column temperature: 40° C.) at a flow rate of 1 mL/min. It should be noted that the number-average molecular weight (hereinafter, referred to as Mn) and the weight-average molecular weight (hereinafter, referred to as Mw) were expressed as values in terms of polystyrene.

<Synthesis of Component (A)>

Synthesis Example 1

In 96.0 g of PM, 20.9 g of jER-828, 20.0 g, of MCA, and 0.26 g of BTEAC were dissolved, and the resulting solution was allowed to react at 120° C. for 20 hours to obtain a photo-orientation compound (solid-content concentration: 30% by mass) (PA1). The epoxy value of the obtained compound was measured, and it was confirmed that epoxy groups with which all the MCA had reacted disappeared.

Synthesis Example 2

In 171.1 g of PM, 53.2 g of jER-1001, 20.0 g, of MCA, and 0.26 g of BTEAC were dissolved, and the resulting solution was allowed to react at 120° C. for 20 hours to obtain a photo-orientation compound (solid-content concentration: 30% by mass) (PA2). The epoxy value of the obtained compound was measured, and it was confirmed that epoxy groups with which all the MCA had reacted disappeared.

Synthesis Example 3

In 89.3 g of PM, 18.0 g of jER-828, 20.0 g, of PCA, and 0.22 g of BTEAC were dissolved, and the resulting solution was allowed to react at 120° C. for 20 hours to obtain a photo-orientation compound (solid-content concentration: 30% by mass) (PA3). The epoxy value of the obtained compound was measured, and it was confirmed that epoxy groups with which all the PCA had reacted disappeared.

Synthesis Example 4

In 96.3 g of PM, 20.9 g of jER-828, 20.0 g, of MeCA, and 0.28 g of BTEAC were dissolved, and the resulting solution was allowed to react at 120° C. for 20 hours to obtain a photo-orientation compound (solid-content concentration: 30% by mass) (PA4). The epoxy value of the obtained compound was measured, and it was confirmed that epoxy groups with which all the MeCA had reacted disappeared.

Synthesis Example 5

In 95.1 g of PM, 20.5 g of jER-828, 20.0 g, of FCA, and 0.27 g of BTEAC were dissolved, and the resulting solution was allowed to react at 120° C. for 20 hours to obtain a photo-orientation compound (solid-content concentration: 30% by mass) (PA5). The epoxy value of the obtained compound was measured, and it was confirmed that epoxy groups with which all the FCA had reacted disappeared.

Synthesis Example 6

In 73.2 g of PM, 11.1 g of TEPIC-L, 20.0 g, of MCA, and 0.26 g of BTEAC were dissolved, and the resulting solution was allowed to react at 120° C. for 20 hours to obtain a photo-orientation compound (solid-content concentration: 30% by mass) (PA6). The epoxy value of the obtained compound was measured, and it was confirmed that epoxy groups with which all the MCA had reacted disappeared.

Synthesis Example 7

In 101.0 g of PM, 23.0 g of jER-828, 20.0 g, of CA, and 0.31 g of BTEAC were dissolved, and the resulting solution was allowed to react at 120° C. for 20 hours to obtain a photo-orientation compound (solid-content concentration: 30% by mass) (PA7). The epoxy value of the obtained compound was measured, and it was confirmed that epoxy groups with which all the CA had reacted disappeared.

Synthesis Example 8

In 78.6 g of PM, 13.4 g of TEPIC-L, 20.0 g, of CA, and 0.31 g of BTEAC were dissolved, and the resulting solution was allowed to react at 120° C. for 20 hours to obtain a photo-orientation compound (solid-content concentration: 30% by mass) (PA8). The epoxy value of the obtained compound was measured, and it was confirmed that epoxy groups with which all the CA had reacted disappeared.

<Synthesis of Component (B)>

Synthesis Example 9

In 48.4 g of PM, 25.0 g of BMAA and 1.04 g of AIBN as a polymerization catalyst were dissolved, and the resulting solution was allowed to react at 85° C. for 20 hours to obtain an acrylic copolymer solution (solid-content concentration: 35% by mass) (PB1). The Mn of the obtained acrylic copolymer was 4,800, and the Mw thereof was 3,100.

<Synthesis of Component (C)>

Synthesis Example 10

In 450.0 g of PM, 100.0 g of MMA, 11.1 g of HEMA, and 5.6 g of AIBN as a polymerization catalyst were dissolved, and the resulting solution was allowed to react at 80° C. for 20 hours to obtain an acrylic copolymer solution (solid-content concentration: 20% by mass) (PC1). The Mn of the obtained acrylic copolymer was 4,200, and the Mw thereof was 7,600.

Examples, Comparative Example

Cured-film formation compositions of Examples and Comparative Example were prepared in accordance with the formulations shown in Table 1. Next, cured films were formed using the individual cured-film formation compositions, and the orientation properties of the thus-obtained cured films were evaluated.

TABLE 1

|  | Component (A) Type Blending Amount (part by mass) | Component (B) Type Blending Amount (part by mass) | Component (C) Type Blending Amount (part by mass) | Component (D) Type Blending Amount (part by mass) | Solvent Type | Solid Content Concentration (% by mass) | Substrate |
|---|---|---|---|---|---|---|---|
| Example 1 | PA1 30 | PB1 100 |  | PTSA 4 | PM | 5 | TAC |
| Example 2 | PA1 60 | PB1 70 |  | PTSA 4 | PM | 5 | TAC |
| Example 3 | PA1 100 | PB1 30 |  | PTSA 4 | PM | 5 | TAC |
| Example 4 | PA2 30 | PB1 100 |  | PTSA 4 | PM | 5 | TAC |
| Example 5 | PA2 60 | PB1 70 |  | PTSA 4 | PM | 5 | TAC |
| Example 6 | PA2 100 | PB1 30 |  | PTSA 4 | PM | 5 | TAC |
| Example 7 | PA2 100 | HMM 30 |  | PTSA 4 | PM | 5 | TAC |
| Example 8 | PA1 30 | PB1 100 |  | PTSA 4 | PM | 5 | Glass |
| Example 9 | PA3 30 | PB1 100 |  | PTSA 4 | PM | 5 | Glass |
| Example 10 | PA4 30 | PB1 100 |  | PTSA 4 | PM | 5 | Glass |
| Example 11 | PA5 30 | PB1 100 |  | PTSA 4 | PM | 5 | Glass |
| Example 12 | PA2 30 | PB1 100 |  | PTSA 4 | PM | 5 | Glass |

TABLE 1-continued

| | Component (A) Type Blending Amount (part by mass) | Component (B) Type Blending Amount (part by mass) | Component (C) Type Blending Amount (part by mass) | Component (D) Type Blending Amount (part by mass) | Solvent Type | Solid Content Concentration (% by mass) | Substrate |
|---|---|---|---|---|---|---|---|
| Example 13 | PA6 30 | PB1 100 | | PTSA 4 | PM | 5 | Glass |
| Example 14 | PA1 25 | PB1 50 | PC1 100 | PTSA 4 | PM | 5 | Glass |
| Example 15 | PA1 25 | HMM 50 | PC1 100 | PTSA 4 | PM | 5 | Glass |
| Example 16 | PA7 30 | PB1 100 | | PTSA 4 | PM | 5 | TAC |
| Example 17 | PA7 30 | PB1 100 | | PTSA 4 | PM | 5 | Glass |
| Example 18 | PA8 30 | PB1 100 | | PTSA 4 | PM | 5 | Glass |
| Comparative Example 1 | PA1 100 | | | PTSA 4 | PM | 5 | Glass |

[Evaluation of Orientation Properties]

Examples 1 to 7, 16

Onto a TAC film, each of the cured-film formation compositions of Examples 1 to 7 and was applied using a bar coater in a wet film thickness of 4 μm. Subsequently, each of the resulting coatings was heated and dried at a temperature of 110° C. for 60 seconds in a heat circulation oven to form a cured film on the corresponding one of the substrates. Each cured film was vertically irradiated with linear polarized light of 313 nm at an exposure amount of 5 mJ/cm$^2$ or 20 mJ/cm$^2$ to form an orientation material. Onto the orientation material on the substrate, a polymerizable liquid crystal solution for horizontal orientation was applied using a bar coater, and subsequently, the resulting coating was prebaked on a hot plate at 70° C. for 60 seconds to form a coating having a film thickness of 1.0 μm. This coating on the substrate was exposed at 300 mJ/cm$^2$ to produce a retardation material. The produced retardation material on the substrate was sandwiched between a pair of polarizing plates, and emergence of retardation properties in the retardation material was observed. In the columns "Orientation Properties", "○" is given to retardation materials in which retardation properties emerged without failure, and "x" is given to retardation materials in which retardation properties did not emerge. The evaluation results are summarized in Table 2 below.

Examples 8 to 15, 17 to 18, Comparative Example 1

On an alkali-free glass, each of the cured-film formation compositions of Examples 8 to 15, and 17 to 18 and Comparative Example 1 was applied using a spin coater in a film thickness of 200 nm. Subsequently, each of the resulting coatings was heated and dried at a temperature of 100° C. for 60 seconds on a hot plate to form a cured film on the corresponding one of the substrates. Each cured film was vertically irradiated with linear polarized light of 313 nm at an exposure amount of 5 mJ/cm$^2$ or 20 mJ/cm$^2$ to form an orientation material. Onto the orientation material on the substrate, a polymerizable liquid crystal solution for horizontal orientation was applied using a spin coater, and subsequently, the resulting coating was prebaked on a hot plate at 65° C. for 60 seconds to form a coating having a film thickness of 1.0 μm. This coating on the substrate was exposed at 300 mJ/cm$^2$ to produce a retardation material. The produced retardation material on the substrate was sandwiched between a pair of polarizing plates, and emergence of retardation properties in the retardation material was observed. In the columns "Orientation Properties", "○" is given to retardation materials in which retardation properties emerged without failure, and "X" is given to retardation materials in which retardation properties did not emerge. The evaluation results are summarized in Table 2 below.

TABLE 2

| | Orientation Properties | | |
|---|---|---|---|
| | 5 mJ/cm$^2$ | 20 mJ/cm$^2$ | Substrate |
| Example 1 | ○ | ○ | TAC |
| Example 2 | ○ | ○ | TAC |
| Example 3 | ○ | ○ | TAC |
| Example 4 | ○ | ○ | TAC |
| Example 5 | ○ | ○ | TAC |
| Example 6 | ○ | ○ | TAC |
| Example 7 | ○ | ○ | TAC |
| Example 8 | ○ | ○ | Glass |
| Example 9 | ○ | ○ | Glass |
| Example 10 | ○ | ○ | Glass |
| Example 11 | ○ | ○ | Glass |
| Example 12 | ○ | ○ | Glass |
| Example 13 | ○ | ○ | Glass |
| Example 14 | ○ | ○ | Glass |
| Example 15 | ○ | ○ | Glass |
| Example 16 | X | ○ | TAC |
| Example 17 | X | ○ | Glass |
| Example 18 | X | ○ | Glass |
| Comparative Example 1 | X | X | Glass |

The cured-film formation compositions of Examples 1 to 15 allowed individual retardation materials to be formed at a low exposure amount of 5 mJ/cm$^2$. The cured-film formation compositions of Examples 16 to 18 allowed individual retardation materials to be formed at an exposure amount of 20 mJ/cm$^2$. In contrast, the cured-film formation composition of Comparative Example 1 did not allow liquid-crystal orientation properties to be obtained.

The invention claimed is:

1. A retardation material obtained by laminating a layer of cured polymerizable liquid crystal on an orientation material obtained by irradiating a cured product of a cured film-formation composition with polarized light, the cured-film formation composition comprising:

a component (A) that is a compound obtained by reacting a cinnamic acid compound of Formula (1) below with a compound having a molecular weight of 100 to 5,000 g/mol and having at least one epoxy group in one molecule,

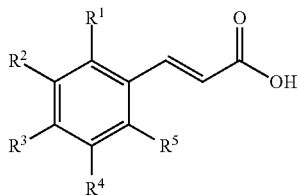

(1)

wherein $R^1$, $R^2$, $R^3$, $R^4$, and $R^5$ are each independently a substituent selected from a hydrogen atom, a halogen atom, a $C_{1-6}$ alkyl, a $C_{1-6}$ haloalkyl, a $C_{1-6}$ alkoxy, a $C_{1-6}$ haloalkoxy, a $C_{3-8}$ cycloalkyl, a $C_{3-8}$ halocycloalkyl, a $C_{2-6}$ alkenyl, a $C_{2-6}$ haloalkenyl, a $C_{3-8}$ cycloalkenyl, a $C_{3-8}$ halocycloalkenyl, a $C_{2-6}$ alkynyl, a $C_{2-6}$ haloalkynyl, a ($C_{1-6}$ alkyl) carbonyl, a ($C_{1-6}$ haloalkyl) carbonyl, a ($C_{1-6}$ alkoxy) carbonyl, a ($C_{1-6}$ haloalkoxy) carbonyl, a ($C_{1-6}$ alkylamino) carbonyl, a ($C_{1-6}$ haloalkyl) aminocarbonyl, a di($C_{1-6}$ alkyl) aminocarbonyl, cyano, and nitro;

a component (B) that is a cross-linking agent; and a component (D) that is a cross-linking catalyst.

2. The retardation material according to claim 1, wherein the cross-linking agent as the component (B) is a cross-linking agent having a methylol group or an alkoxymethyl group.

3. The retardation material according to claim 1, further comprising a component (C) that is a polymer having a thermally cross-linkable group.

4. The retardation material according to claim 1, wherein the composition contains the component (B) in an amount of 1 part by mass to 600 parts by mass based on 100 parts by mass of the component (A).

5. The retardation material according to claim 3, wherein the composition contains the component (C) in an amount of 1 part by mass to 400 parts by mass based on 100 parts by mass of a total amount of the component (A) and the component (B) as a cross-linking agent.

6. The retardation material according to claim 4, wherein the composition contains the component (D) in an amount of 0.01 part by mass to 20 parts by mass based on 100 parts by mass of a total amount of the component (A) and the component (B) as a cross-linking agent.

7. The retardation material according to claim 1, wherein the orientation material has a thickness of 0.05 μm to 5 μm.

8. A retardation material, the retardation material being formed by applying and orienting a polymerizable liquid crystal solution on an orientation material, and curing the polymerizable liquid crystal solution in the oriented state to form the retardation material; wherein the orientation material is a cured product of a cured-film formation composition, the cured-film formation composition comprising:

a component (A) that is a compound obtained by reacting a cinnamic acid compound of Formula (1) below with a compound having a molecular weight of 100 to 5,000 g/mol and having at least one epoxy group in one molecule,

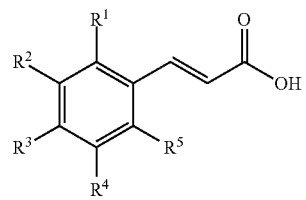

(1)

wherein $R^1$, $R^2$, $R^3$, $R^4$, and $R^5$ are each independently a substituent selected from a hydrogen atom, a halogen atom, a $C_{1-6}$ alkyl, a $C_{1-6}$ haloalkyl, a $C_{1-6}$ alkoxy, a $C_{1-6}$ haloalkoxy, a $C_{3-8}$ cycloalkyl, a $C_{3-8}$ halocycloalkyl, a $C_{2-6}$ alkenyl, a $C_{2-6}$ haloalkenyl, a $C_{3-8}$ cycloalkenyl, a $C_{3-8}$ halocycloalkenyl, a $C_{2-6}$ alkynyl, a $C_{2-6}$ haloalkynyl, a ($C_{1-6}$ alkyl) carbonyl, a ($C_{1-6}$ haloalkyl) carbonyl, a ($C_{1-6}$ alkoxy) carbonyl, a ($C_{1-6}$ haloalkoxy) carbonyl, a ($C_{1-6}$ alkylamino) carbonyl, a ($C_{1-6}$ haloalkyl) aminocarbonyl, a di($C_{1-6}$ alkyl) aminocarbonyl, cyano, and nitro;

a component (B) that is a cross-linking agent;
a component (C) that is a polymer having a thermally cross-linkable group; and
a component (D) that is a cross-linking catalyst.

9. The retardation material according to claim 8, wherein the retardation material is formed as a layer having optical anisotropy.

* * * * *